(12) United States Patent
Kaneko

(10) Patent No.: US 10,942,190 B2
(45) Date of Patent: Mar. 9, 2021

(54) MEASUREMENT METHOD FOR AMYLOID PRECURSOR PROTEIN CLEAVAGE PEPTIDES

(71) Applicant: SHIMADZU CORPORATION, Kyoto (JP)

(72) Inventor: Naoki Kaneko, Kyoto (JP)

(73) Assignee: Shimadzu Corporation, Kyoto (JP)

(*) Notice: Subject to any disclaimer, the term of this patent is extended or adjusted under 35 U.S.C. 154(b) by 387 days.

(21) Appl. No.: 15/112,916

(22) PCT Filed: Jan. 7, 2015

(86) PCT No.: PCT/JP2015/050255
§ 371 (c)(1),
(2) Date: Jul. 20, 2016

(87) PCT Pub. No.: WO2015/111430
PCT Pub. Date: Jul. 30, 2015

(65) Prior Publication Data
US 2016/0334420 A1    Nov. 17, 2016

(30) Foreign Application Priority Data
Jan. 21, 2014 (JP) .............................. JP2014-009010

(51) Int. Cl.
*G01N 33/68* (2006.01)
(52) U.S. Cl.
CPC . *G01N 33/6896* (2013.01); *G01N 2333/4709* (2013.01); *G01N 2560/00* (2013.01); *G01N 2800/2821* (2013.01)
(58) Field of Classification Search
CPC ....... G01N 2333/4709; G01N 2560/00; G01N 2800/2821; G01N 33/6896
See application file for complete search history.

(56) References Cited

U.S. PATENT DOCUMENTS

| | | |
|---|---|---|
| 2004/0014142 A1 | 1/2004 | Van Mechelen |
| 2005/0221385 A1 | 10/2005 | Nikiforov et al. |
| 2007/0111252 A1* | 5/2007 | Suzuki ............... C07K 14/4711 435/7.1 |
| 2009/0028869 A1 | 1/2009 | Dodel |
| 2010/0086938 A1 | 4/2010 | Shimada |
| 2010/0297662 A1 | 11/2010 | Hoshi |
| 2011/0097319 A1 | 4/2011 | Matsubara |
| 2017/0016910 A1* | 1/2017 | Kaneko ............... G01N 33/6851 |

FOREIGN PATENT DOCUMENTS

| | | |
|---|---|---|
| JP | 2010-019864 A | 1/2010 |
| JP | 2010-515717 A | 5/2010 |
| JP | 2013-63976 A | 4/2013 |
| JP | 2014-020872 A | 2/2014 |
| WO | WO 2008-065806 A1 | 6/2008 |
| WO | WO 2009-057664 A1 | 5/2009 |
| WO | WO 2014-014536 A1 | 1/2014 |

OTHER PUBLICATIONS

Kaneko et al., "Identification and quantification of amyloid beta-related peptides in human plasma using matrix-assisted laser desorption/ionization time-of-flight mass spectrometry," Proc. Jpn. Acad. Ser. B Phys. Biol. Sci., 2014, vol. 90, No. 3 (March), pp. 104-117.*
Wang et al., "The profile of soluble amyloid beta protein in cultured cell media. Detection and quantification of amyloid beta protein and variants by immunoprecipitation-mass spectrometry," J. Biol. Chem., 1996, vol. 271, No. 50, pp. 31894-31902.*
Kuyama et al., "Sensitive detection of phosphopeptides by matrix-assisted laser desorption/ionization mass spectrometry: use of alkylphosphonic acids as matrix additives," Rapid Commun. Mass Spectrom., 2008, vol. 22, pp. 1109-1116.*
Portelius et al., "Characterization of Amyloid β Peptides in Cerebrospinal Fluid by an Automated Immunoprecipitation Procedure Followed by Mass Spectrometry," J. Proteome Res., 2007, vol. 6, No. 11, pp. 4433-4439.*
Gaussier et al., "Replacement of Trifluoroacetic Acid with HCl in the Hydrophobic Purification Steps of Pediocin PA-1: a Structural Effect," Appl. Environ. Microbiol., 2002, vol. 68, No. 10, pp. 4803-4808.*
A printout "n-Dodecyl-beta-Maltoside Detergent" retrieved from https://www.thermofisher.com/order/catalog/product/89902?SID=srch-srp-89902#/ 89902?SID=srch-srp-89902 on Dec. 2, 2019.*
A printout "Nonyl-β-D-1-thiomaltoside" retrieved from https://www.sigmaaldrich.com/catalog/product/sigma/74436?lang=en& region=US on Dec. 2, 2019.*
Japanese Office Action dated Dec. 11, 2018 as issued in corresponding Japanese Application No. 2015-558791 and its English translation thereof.
Blennow et al.; "Alzheimer's disease"; *Lancet*, 368:387-403 (Jul. 2006).

(Continued)

*Primary Examiner* — Galina M. Yakovleva
(74) *Attorney, Agent, or Firm* — Morgan, Lewis & Bockius LLP

(57) ABSTRACT

Provided is a method for measuring amyloid precursor protein (APP) cleavage peptides including amyloid beta (Aβ) peptides. A method for measuring APP cleavage peptides in a blood sample includes the steps of: bringing a blood sample into contact with an antibody-immobilizing carrier in a binding solution to bind the antibody-immobilizing carrier and APP cleavage peptides contained in the blood sample, the antibody-immobilizing carrier including a carrier, and an antibody bound to the carrier and selected from the group consisting of an immunoglobulin having an antigen binding site capable of recognizing APP cleavage peptides and an immunoglobulin fragment containing an antigen binding site capable of recognizing APP cleavage peptides; washing a bound body of the antibody-immobilizing carrier and the APP cleavage peptides using a washing solution; dissociating the APP cleavage peptides from the antibody-immobilizing carrier using an acidic aqueous solution containing an organic solvent; and detecting the dissociated APP cleavage peptides.

20 Claims, 20 Drawing Sheets
Specification includes a Sequence Listing.

(56) References Cited

OTHER PUBLICATIONS

Hampel et al.; "Biological markers of amyloid β-related mechanisms in Alzheimer's disease"; *Exp. Neurol.*, 223(2):334-346 (Jun. 2010).

Kaneko et al.; "Multi Epitope-Targeting Immunoprecipitation Using F(ab') Fragments with High Affinity and Specificity for the Enhanced Detection of a Peptide with Matrix-Assisted Laser Desorption Ionization-Time-of-Flight Mass Spectrometry"; *Anal. Chem.*, 85(6):3152-3159 (Mar. 2013).

Portelius et al.; "Determination of β-Amyloid Peptide Signatures in Cerebrospinal Fluid Using Immunoprecipitation-Mass Spectrometry"; *J. Proteome Res.*, 5(4):1010-1016 (Apr. 2006).

PCT International Search Report issued in application No. PCT/JP2015/050255 dated Apr. 7, 2015.

PCT International Preliminary Report on Patentability issued in application No. PCT/JP2015/050255 dated Jul. 26, 2016.

\* cited by examiner (A) 3mM HCl
(B) 3mM HCl / 50%(v/v) acetonitrile (A) without washing using 0.1% (w/v) OTG / 200mM ammonium acetate buffer solution
(pH7.4)

(B) with washing using 0.1% (w/v) OTG / 200mM ammonium acetate buffer solution
(pH7.4)

(A) 5 mg/mL CHCA solution 0.5 µL, and 2%(w/v) MDPNA 0.5µL
(B) 1.5 mg/mL CHCA solution 0.5µL, and 0.6%(w/v) MDPNA 0.5µL
(C) 0.5 mg/mL CHCA solution 0.5µL, and 0.2%(w/v) MDPNA 0.5µL (A) 5mM HCl
(B) 5mM HCl / 20%(v/v) acetonitrile
(C) 5mM HCl / 25%(v/v) acetonitrile
(D) 5mM HCl / 50%(v/v) acetonitrile
(E) 5mM HCl / 70%(v/v) acetonitrile (A) 6E10/4G8 F(ab') - immobilized beads;
    5mM HCl / 70%(v/v) acetonitrile
(B) Human plasma sample; Cysteine-PEG$_{24}$ beads;
    5mM HCl / 70%(v/v) acetonitrile
(C) Human plasma sample; 6E10/4G8 F(ab') - immobilized beads;
    5mM HCl / 70%(v/v) acetonitrile

Fig.7

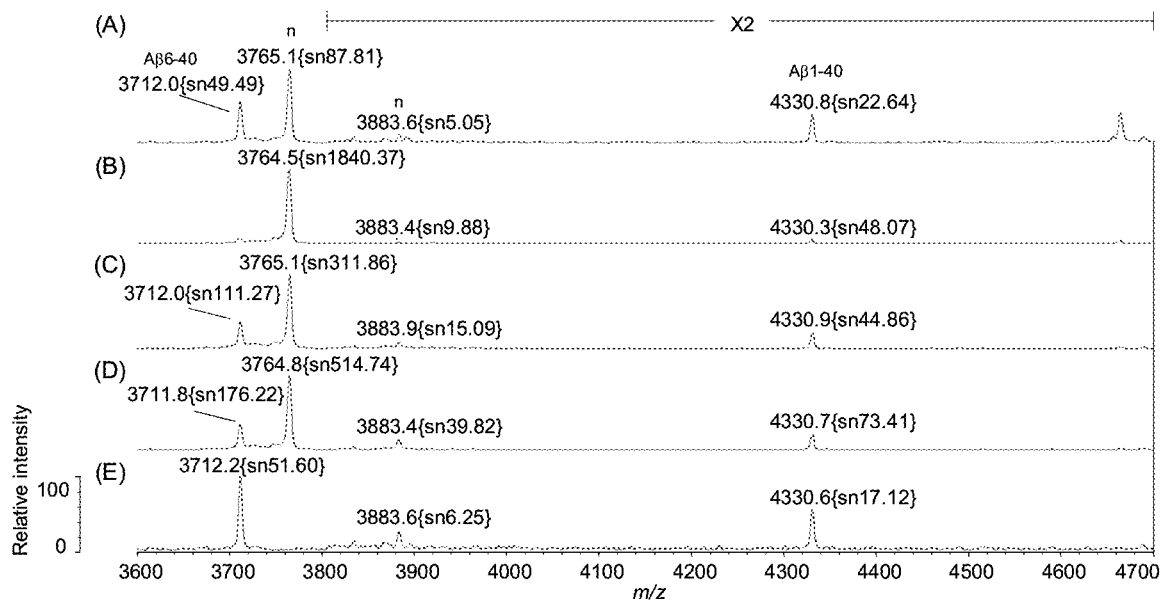

(A) Binding solution:
   1%(w/v) OTG, 800mM GlcNAc, 100mM Tris-HCl, 300mM NaCl, pH7.4;
   Washing solution:
   0.5%(w/v) OTG, 50mM Tris-HCl, 150mM NaCl, pH7.4

(B) Binding solution:
   3%(w/v) OG, 800mM GlcNAc, 100mM Tris-HCl, 300mM NaCl, pH7.4;
   Washing solution:
   1.5%(w/v) OG, 50mM Tris-HCl, 150mM NaCl, pH7.4

(C) Binding solution:
   0.3%(w/v) DM, 800mM GlcNAc, 100mM Tris-HCl, 300mM NaCl, pH7.4;
   Washing solution:
   0.15%(w/v) DM, 50mM Tris-HCl, 150mM NaCl, pH7.4

(D) Binding solution:
   0.03%(w/v) DDM, 800mM GlcNAc, 100mM Tris-HCl, 300mM NaCl, pH7.4;
   Washing solution:
   0.015%(w/v) DDM, 50mM Tris-HCl, 150mM NaCl, pH7.4

(E) Binding solution:
   0.4%(w/v) NTM, 800mM GlcNAc, 100mM Tris-HCl, 300mM NaCl, pH7.4;
   Washing solution:
   0.2%(w/v) NTM, 50mM Tris-HCl, 150mM NaCl, pH7.4

(D-1) Binding solution:
    0.03%(w/v) DDM, 800mM GlcNAc, 100mM Tris-HCl, 300mM NaCl, pH7.4;
Washing solution:
    0.015%(w/v) DDM, 50mM Tris-HCl, 150mM NaCl, pH7.4

(D-2) Binding solution:
    0.1%(w/v) DDM, 800mM GlcNAc, 100mM Tris-HCl, 300mM NaCl, pH7.4;
Washing solution:
    0.05%(w/v) DDM, 50mM Tris-HCl, 150mM NaCl, pH7.4

(D-3) Binding solution:
    0.3%(w/v) DDM, 800mM GlcNAc, 100mM Tris-HCl, 300mM NaCl, pH7.4;
Washing solution:
    0.15%(w/v) DDM, 50mM Tris-HCl, 150mM NaCl, pH7.4

(E-1) Binding solution:
   0.4%(w/v) NTM, 800mM GlcNAc, 100mM Tris-HCl, 300mM NaCl, pH7.4;
   Washing solution:
   0.2%(w/v) NTM, 50mM Tris-HCl, 150mM NaCl, pH7.4

(E-2) Binding solution:
   0.3%(w/v) NTM, 800mM GlcNAc, 100mM Tris-HCl, 300mM NaCl, pH7.4;
   Washing solution:
   0.15%(w/v) NTM, 50mM Tris-HCl, 150mM NaCl, pH7.4

(E-3) Binding solution:
   0.2%(w/v) NTM, 800mM GlcNAc, 100mM Tris-HCl, 300mM NaCl, pH7.4;
   Washing solution:
   0.1%(w/v) NTM, 50mM Tris-HCl, 150mM NaCl, pH7.4

(F) Binding solution:
   0.2%(w/v) DDM, 0.2%(w/v) NTM, 800mM GlcNAc, 100mM Tris-HCl, 300mM NaCl, pH7.4;
   Washing solution:
   0.1%(w/v) DDM, 0.1%(w/v) NTM, 50mM Tris-HCl, 150mM NaCl, pH7.4

(A) Binding solution:
   1%(w/v) OTG, 800mM GlcNAc, 100mM Tris-HCl, 300mM NaCl, pH7.4;
   Washing solution:
   0.5%(w/v) OTG, 50mM Tris-HCl, 150mM NaCl, pH7.4

(A) Binding solution:

2%(w/v) OTG, 800mM GlcNAc, 100mM Tris-HCl, 300mM NaCl, pH7.4;

Washing solution:

1%(w/v) OTG, 50mM Tris-HCl, 150mM NaCl, pH7.4;

Eluent::

5mM HCl (B) Binding solution:

0.2%(w/v) DDM, 0.2%(w/v) NTM, 800mM GlcNAc, 100mM Tris-HCl, 300mM NaCl, pH7.4;

Washing solution:

0.1%(w/v) DDM, 0.1%(w/v) NTM, 50mM Tris-HCl, 150mM NaCl, pH7.4;

Eluent:

5mM HCl / 70%(v/v) acetonitrile

Fig.12
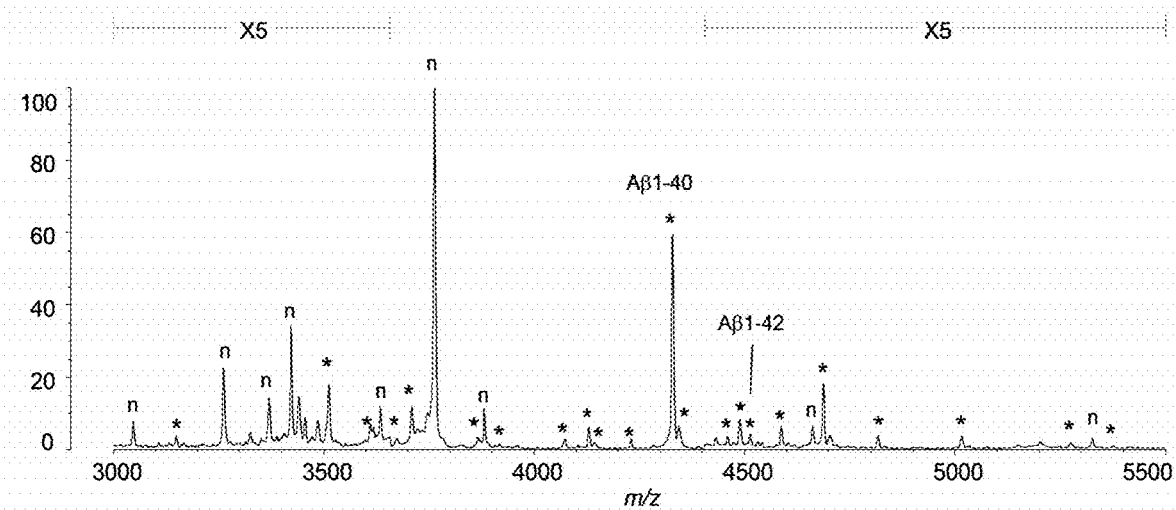
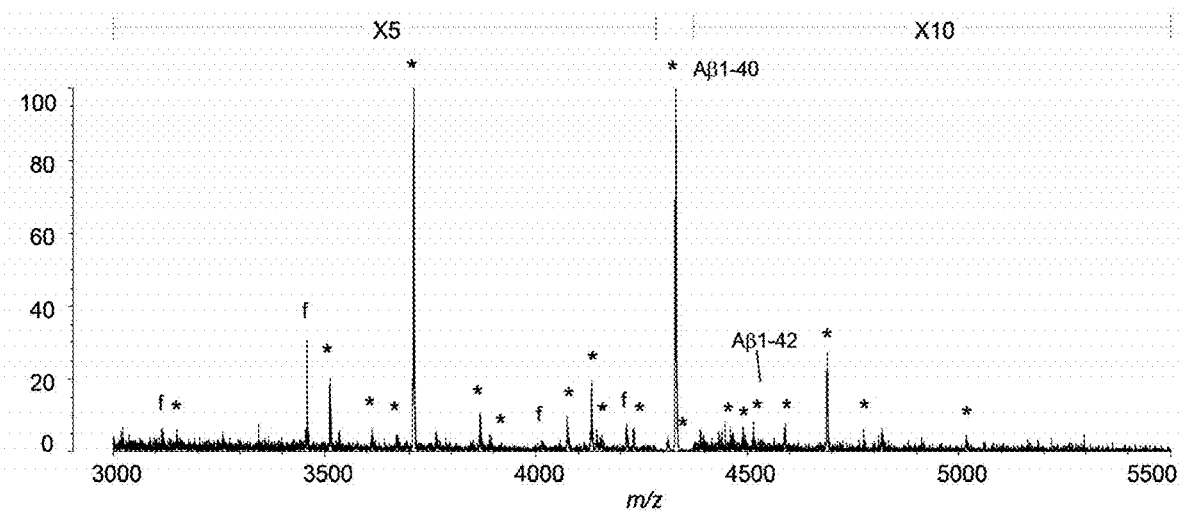

Fig.13
(A) APP682-711/Aβ11-40 (SEQ ID No. 1)
MS/MS
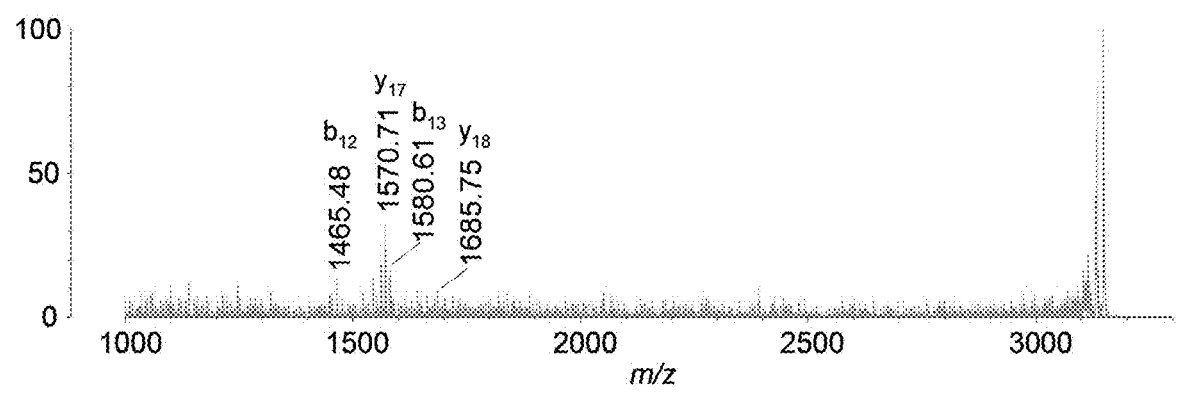
(B) APP677-709/Aβ6-38 (SEQ ID No. 2)
MS/MS
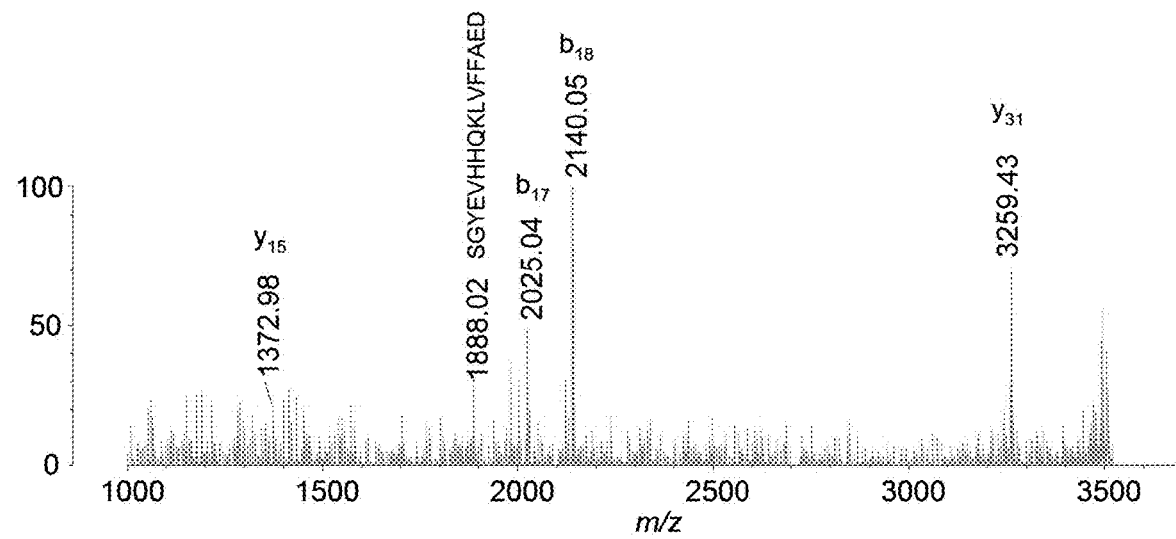

Fig.14
(C) APP676-708/Aβ5-37 (SEQ ID No. 3)
MS/MS
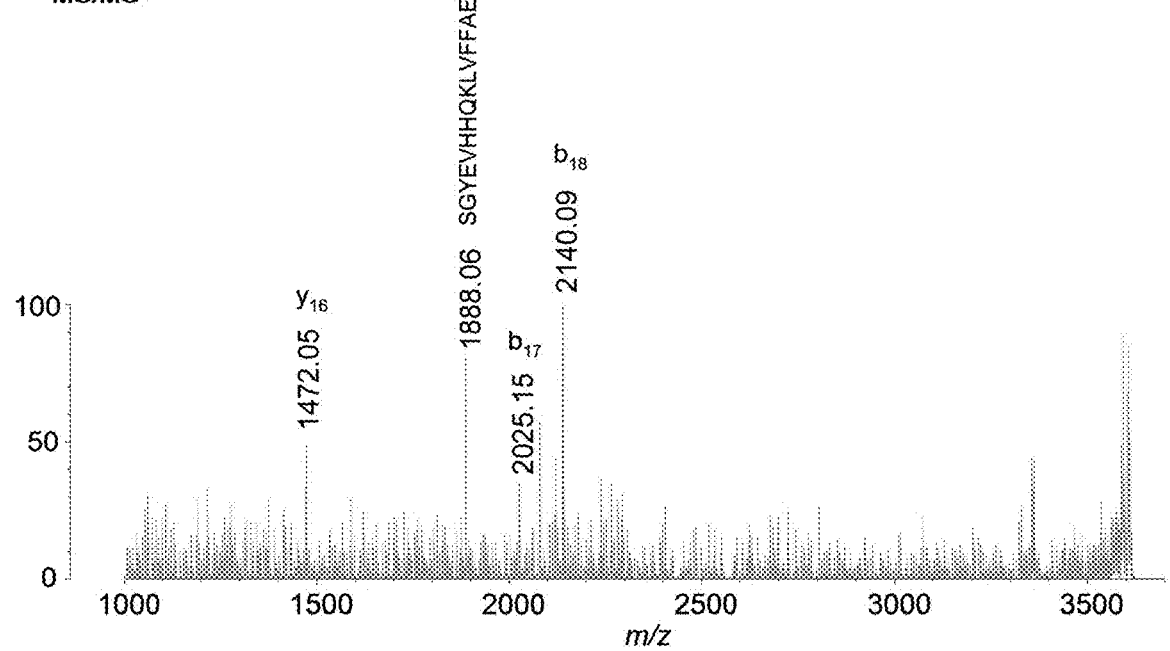
(D) APP672-704/Aβ1-33 (SEQ ID No. 4)
MS/MS
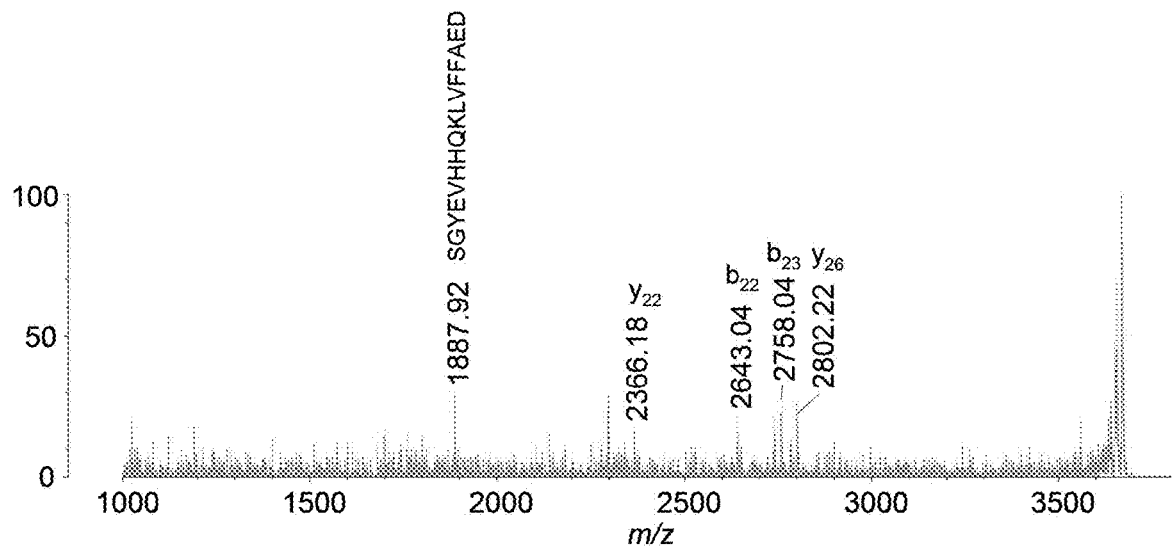

Fig.15
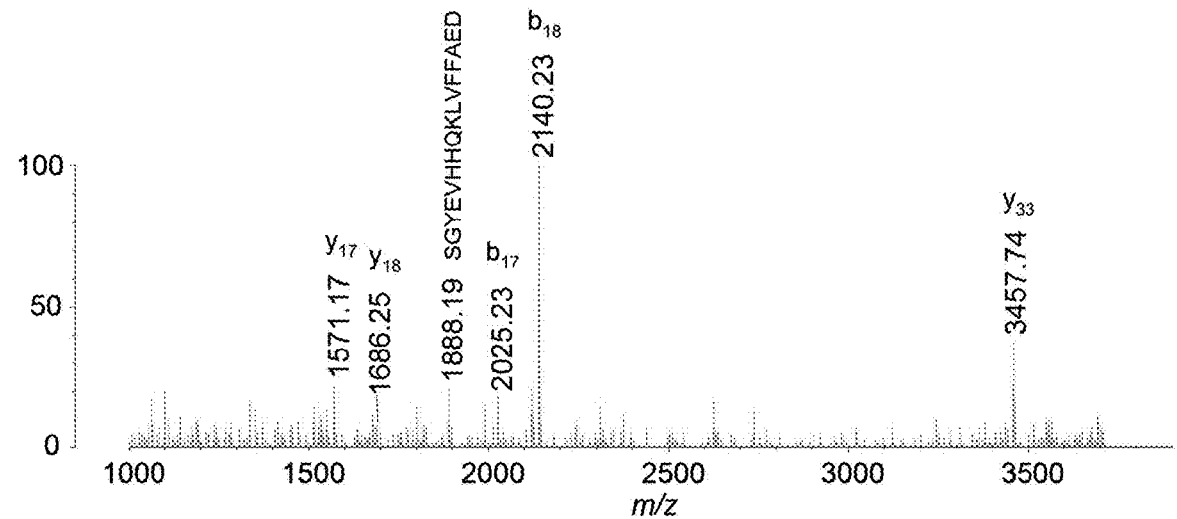
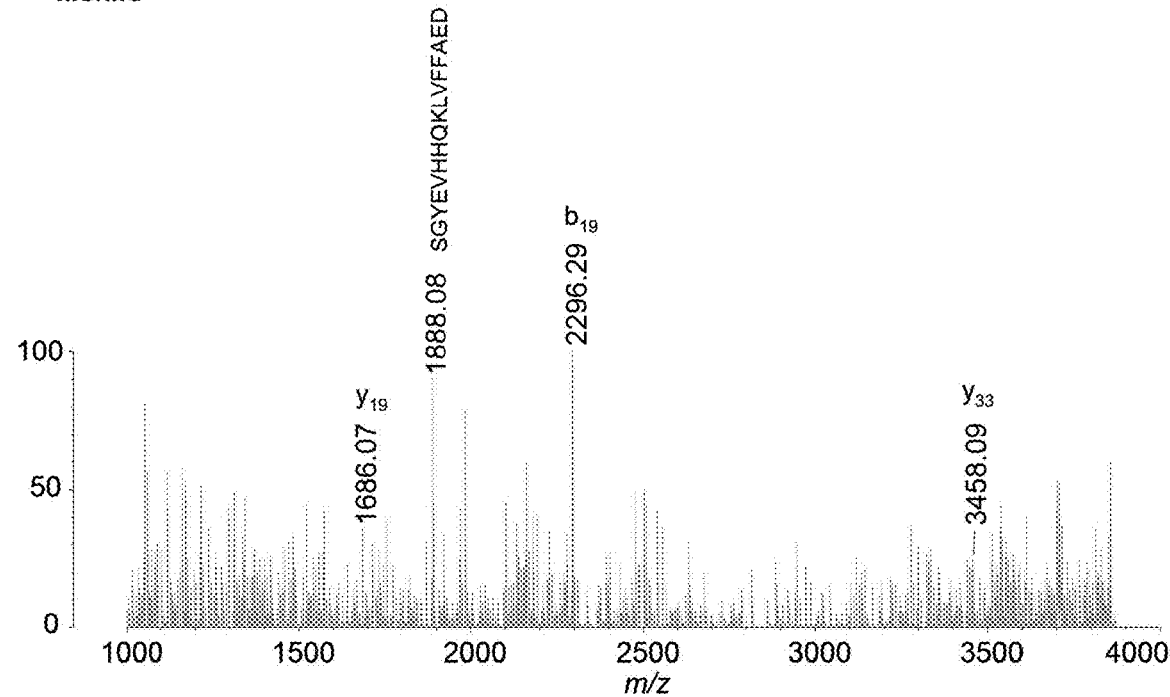

Fig.16
(G) APP672-706/Aβ1-35 (SEQ ID No. 7)
MS/MS
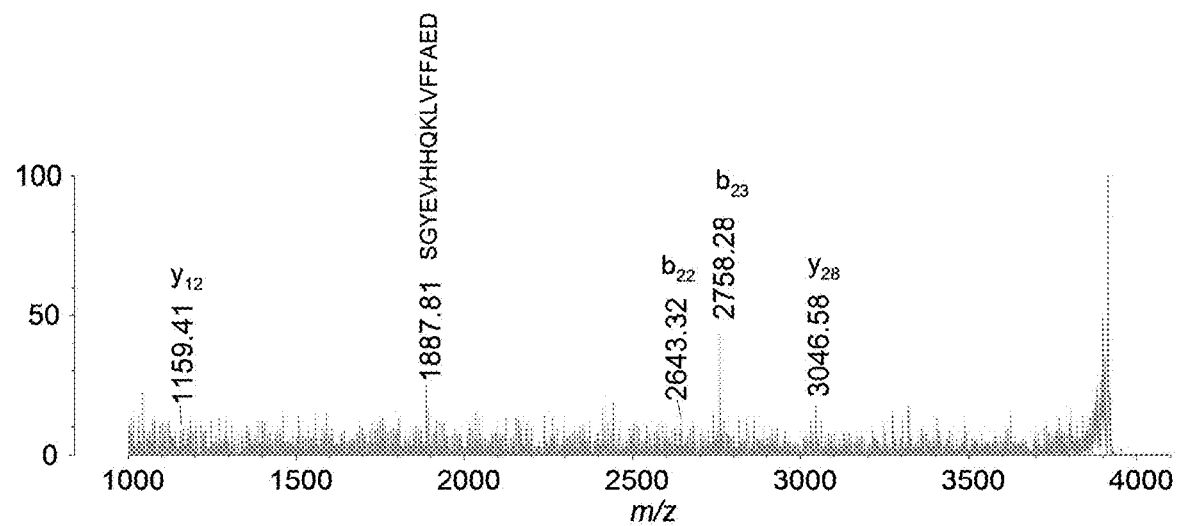
(H) APP672-708/Aβ1-37 (SEQ ID No. 8)
MS/MS
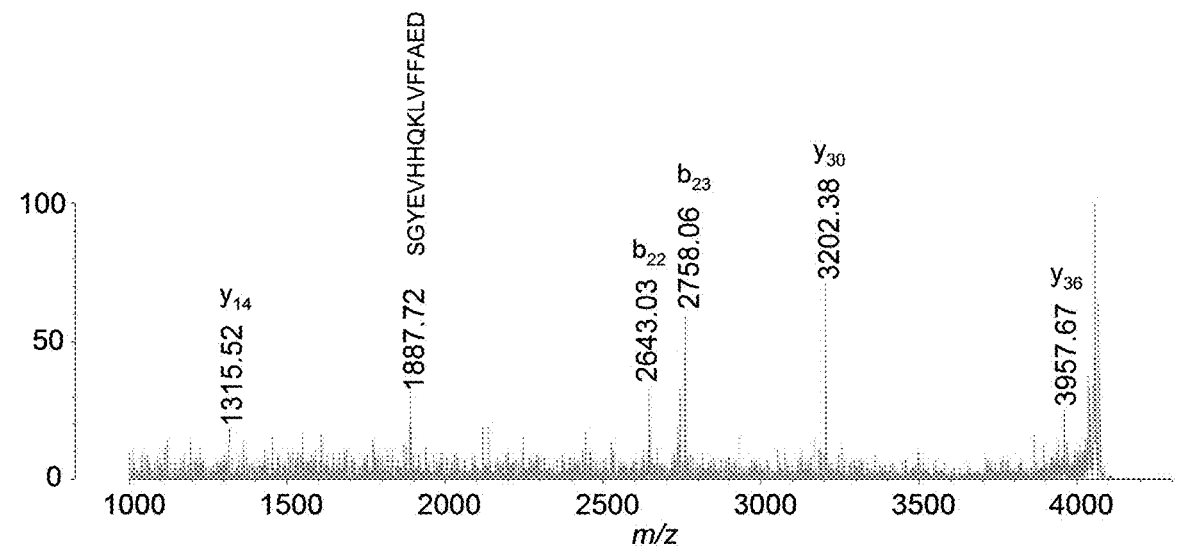

Fig.17
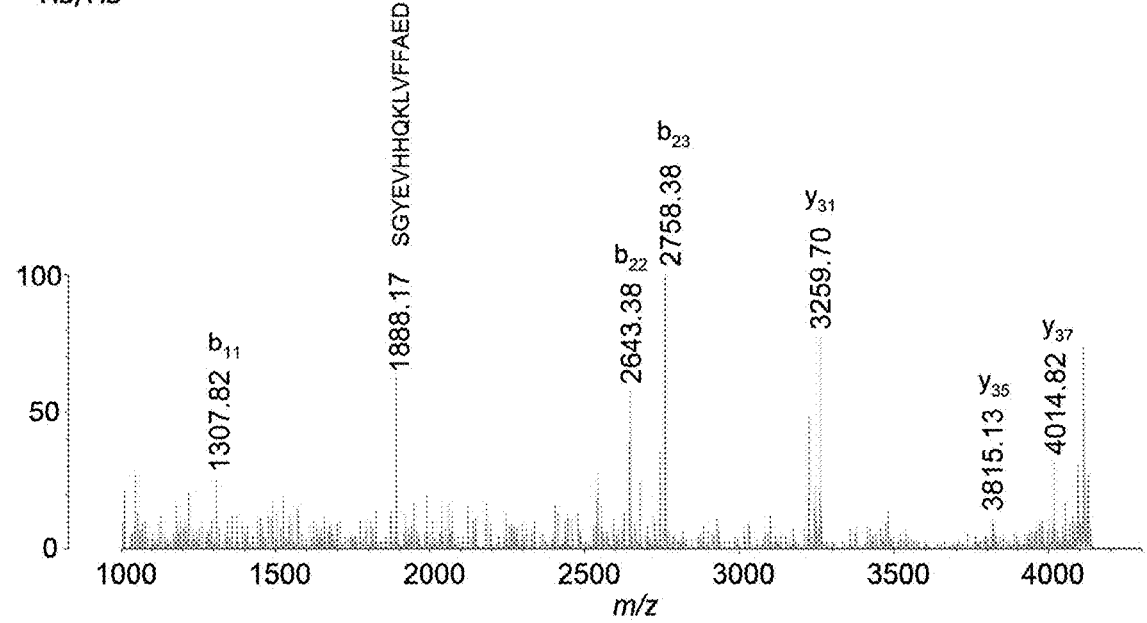
(I) APP672-709/Aβ1-38 (SEQ ID No. 9)
MS/MS
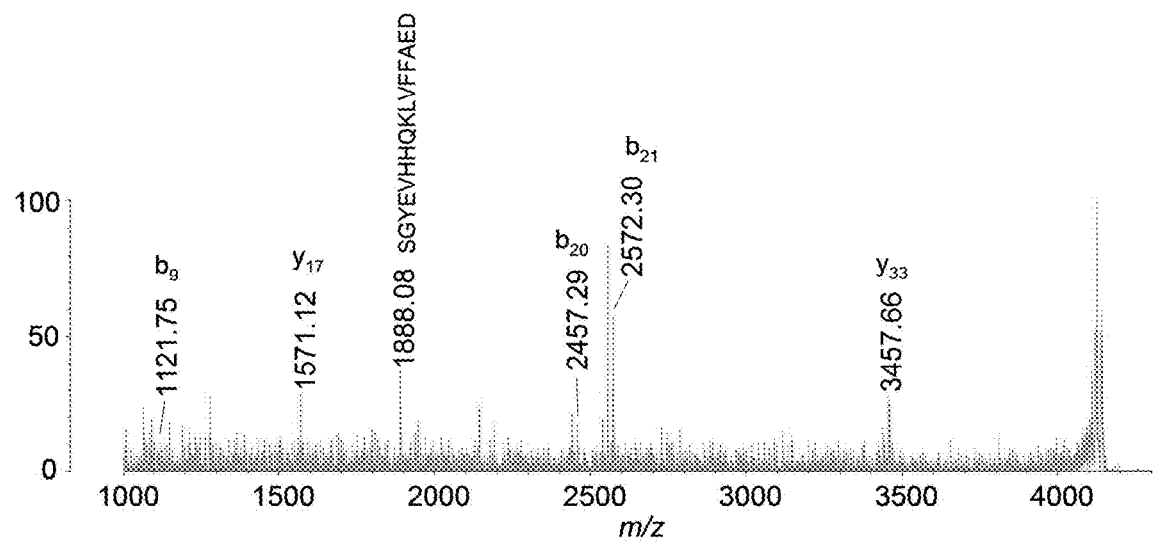
(J) APP674-711/Aβ3-40 (SEQ ID No. 10)
MS/MS Fig.18
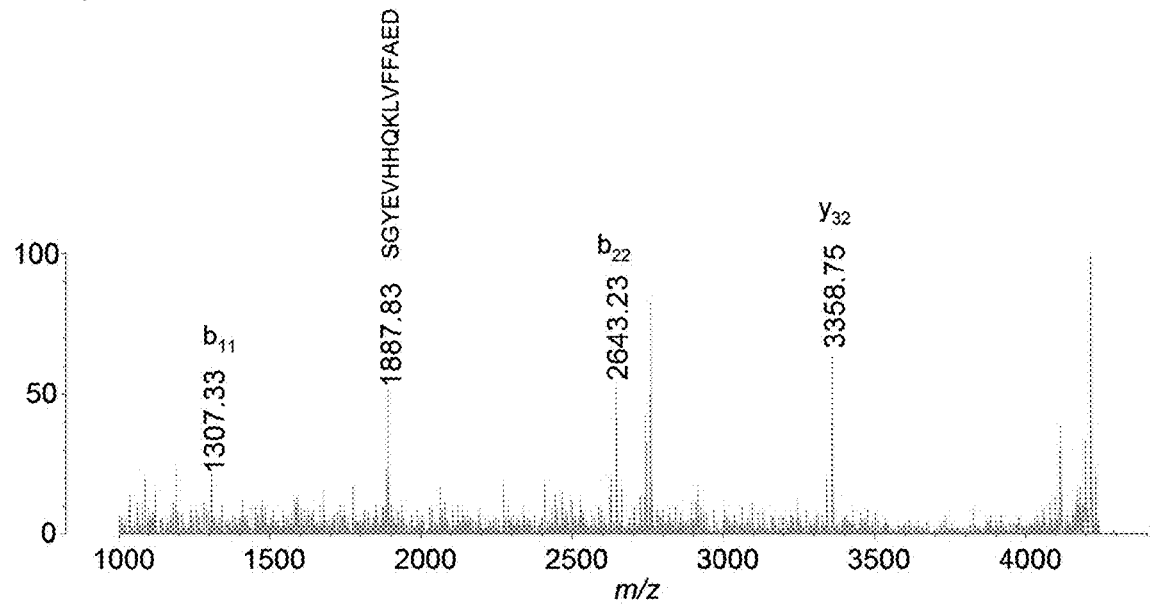
(K) APP672-710/Aβ1-39 (SEQ ID No. 11)
MS/MS
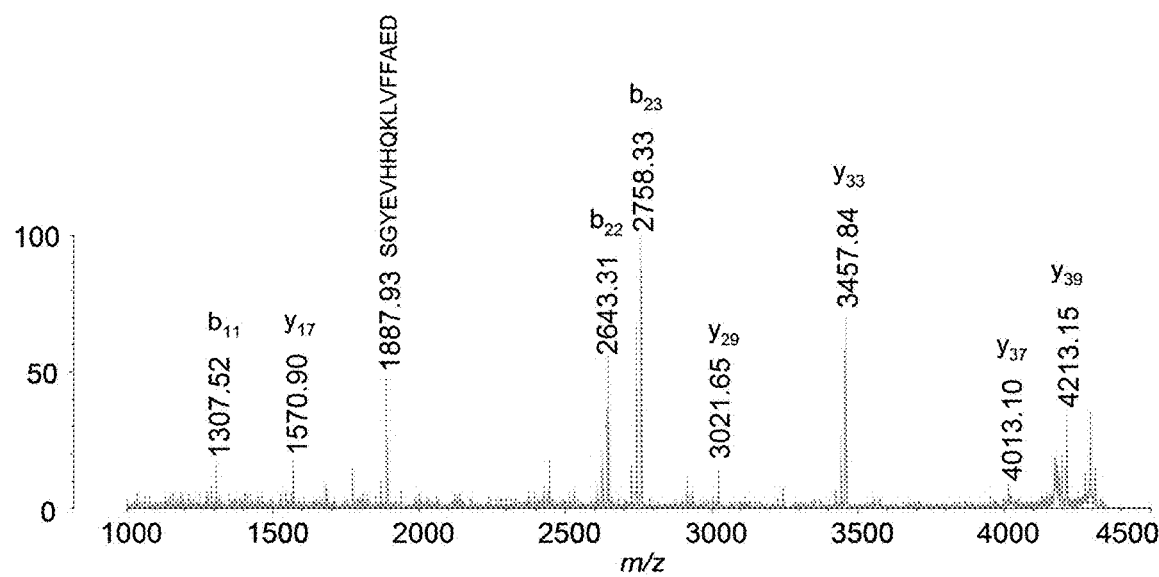
(L) APP672-711/Aβ1-40 (SEQ ID No. 12)
MS/MS Fig.19
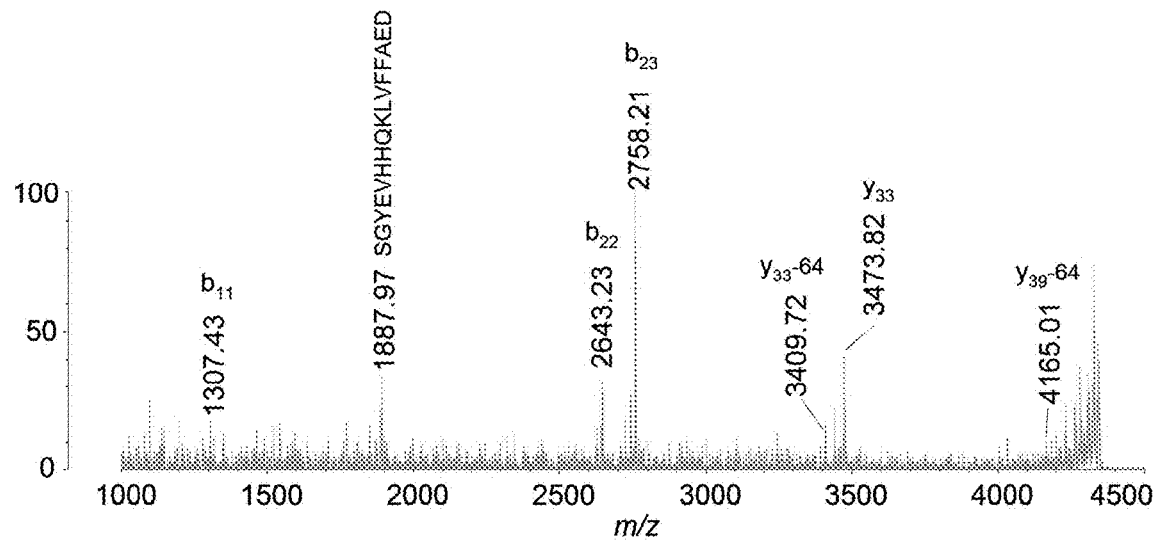
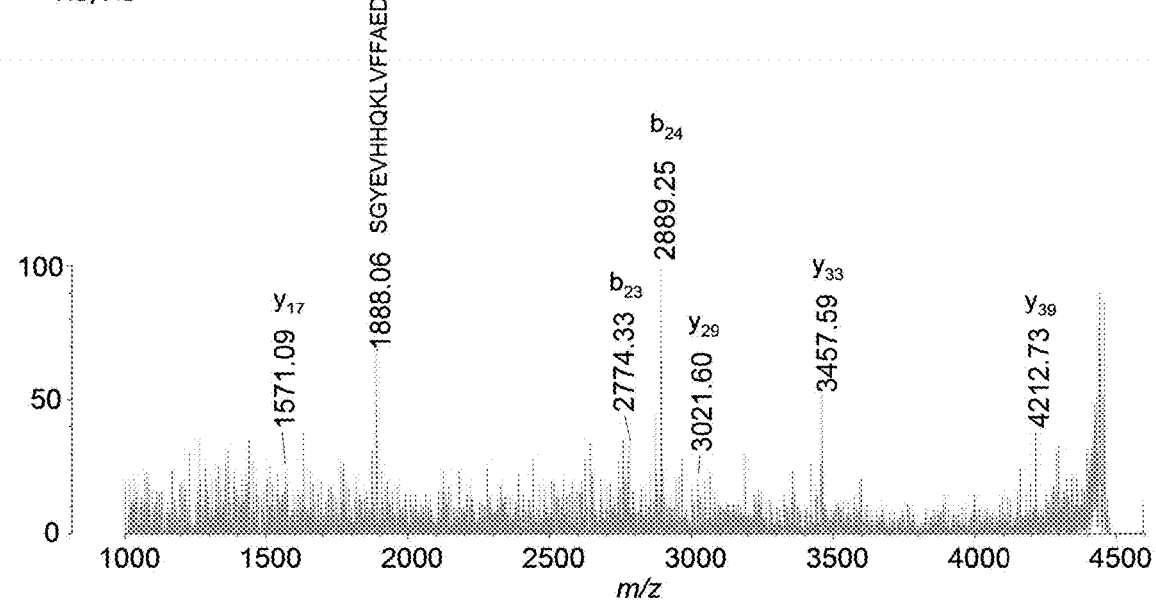

Fig.20
(O) APP669-709 (SEQ ID No. 15)
MS/MS
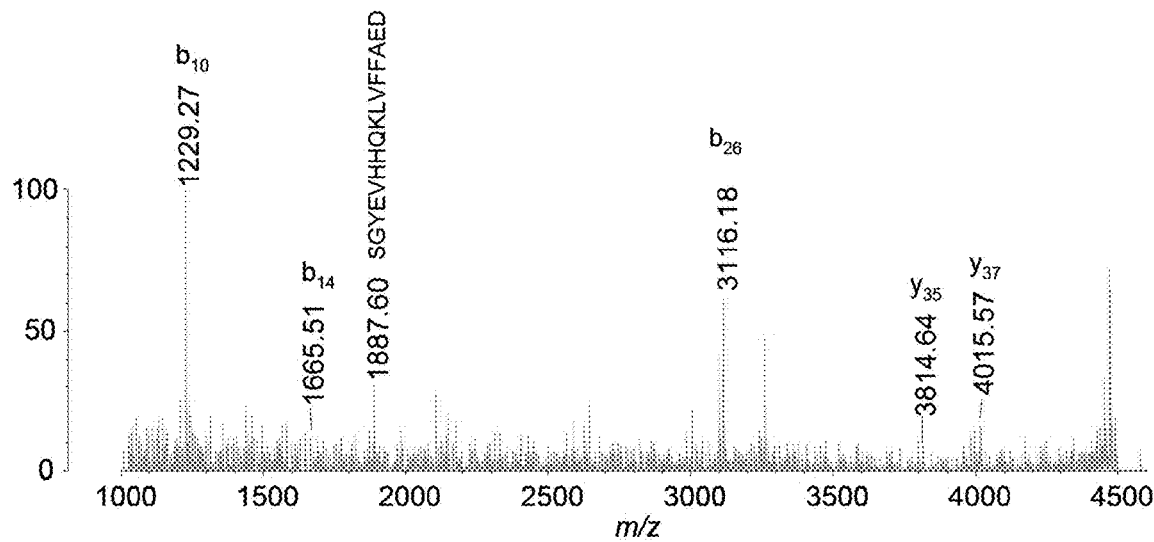
(P) APP676-713/Aβ1-42 (SEQ ID No. 16)
MS/MS
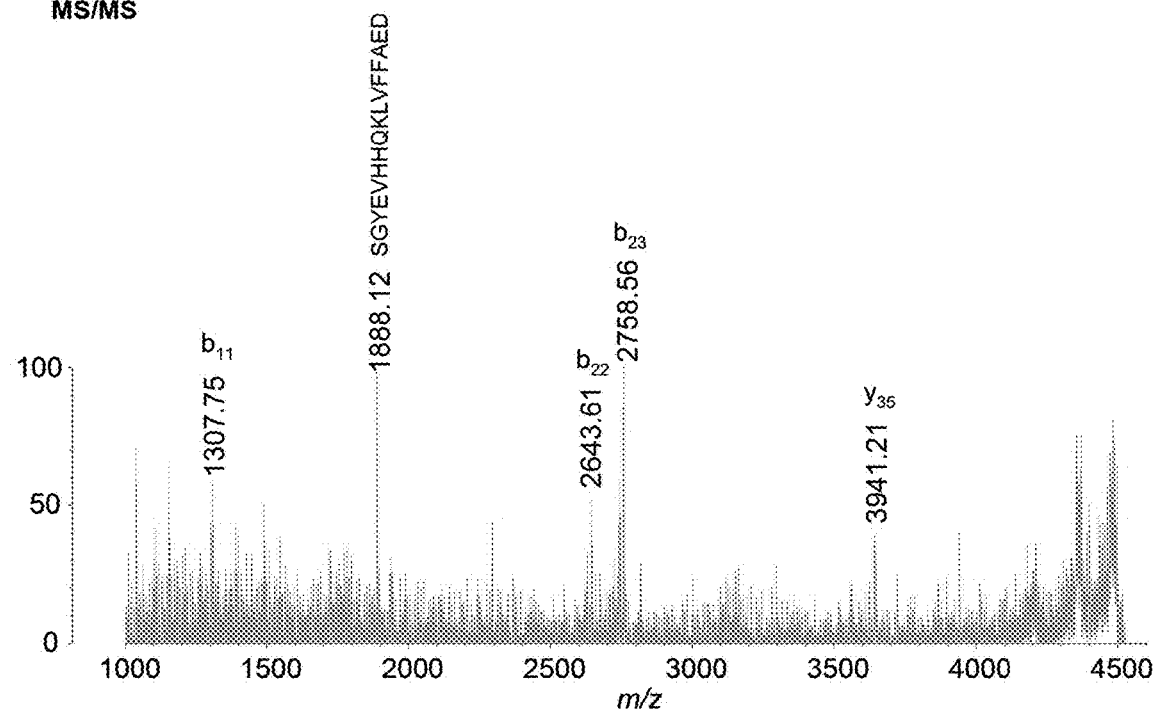

Fig.21
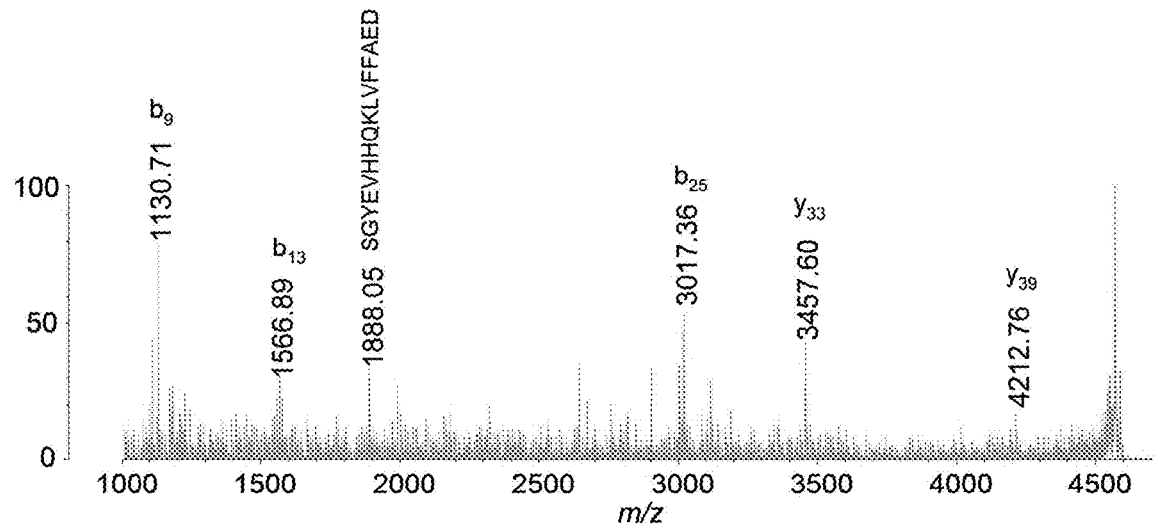
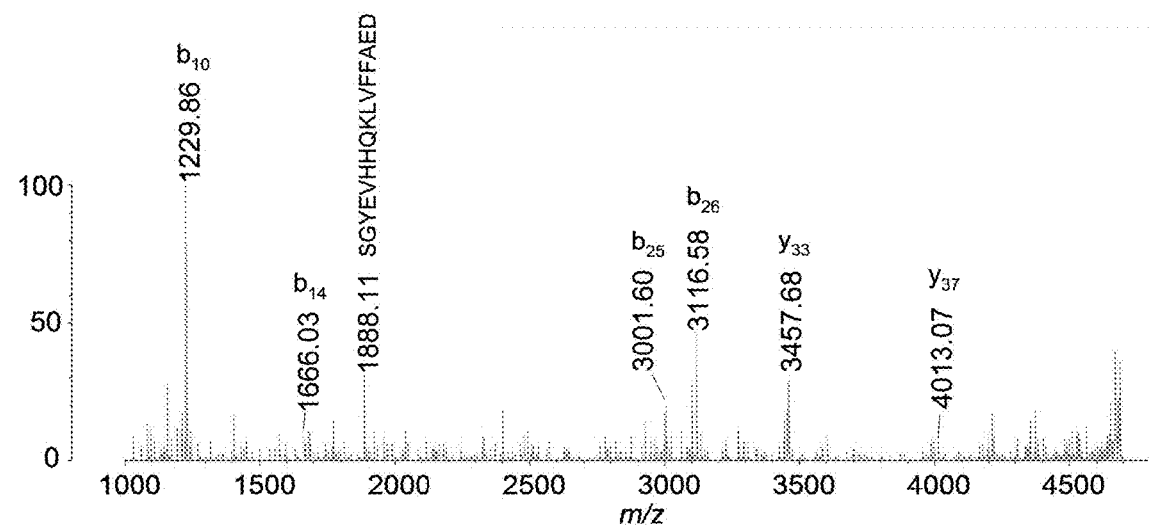

Fig.22
(S) APP666-709 (SEQ ID No. 19)
MS/MS
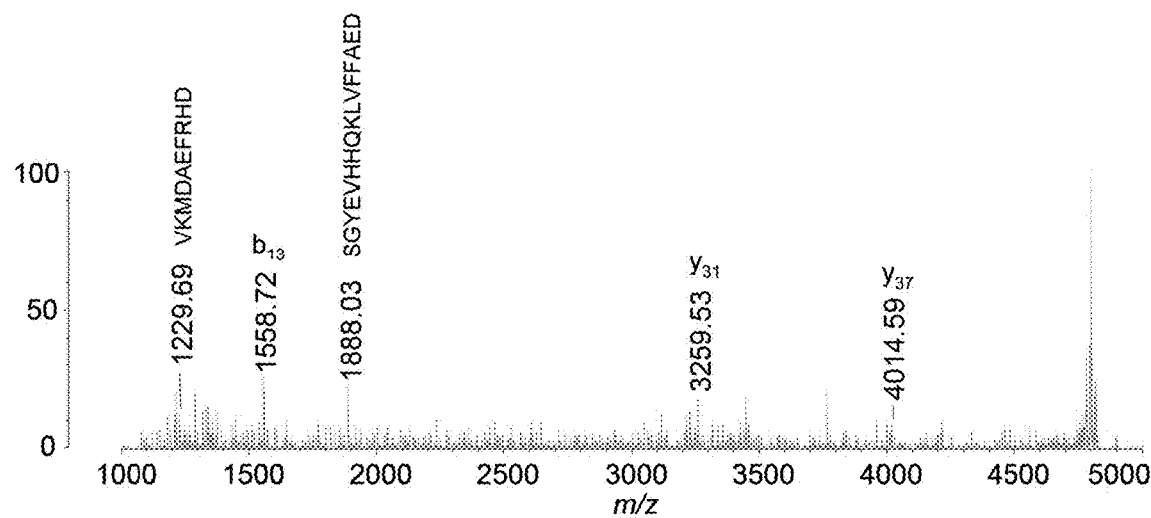
(T) APP666-711 (SEQ ID No. 20)
MS/MS
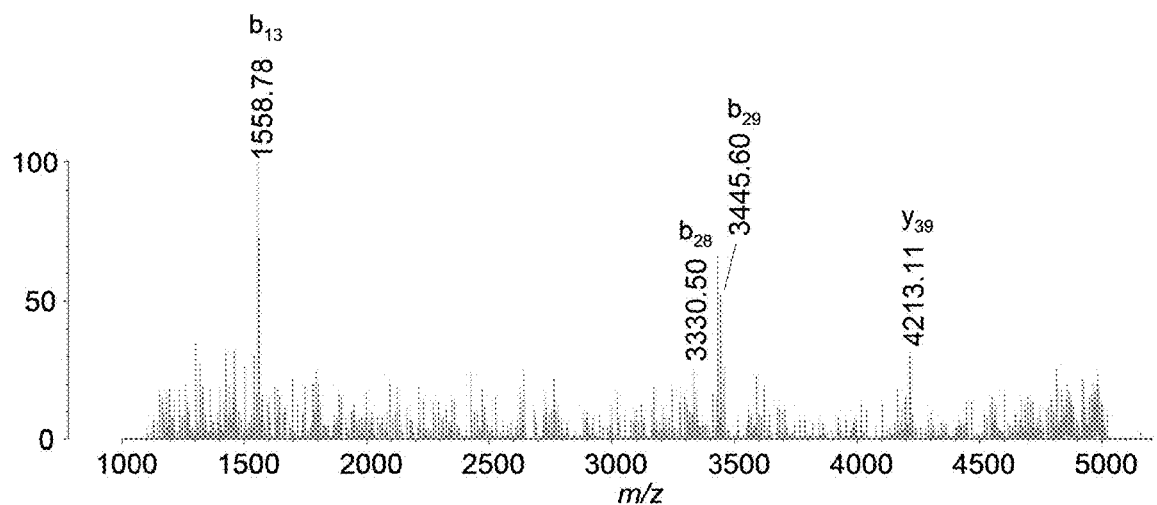

SEQUENCE LISTING

<160> NUMBER OF SEQ ID NOS: 22

<210> SEQ ID NO 1
<211> LENGTH: 30
<212> TYPE: PRT
<213> ORGANISM: Homo Sapiens

<400> SEQUENCE: 1

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 2
<211> LENGTH: 33
<212> TYPE: PRT
<213> ORGANISM: Homo Sapiens

<400> SEQUENCE: 2

His Asp Ser Gly Tyr Glu Val His His Gln Lys Leu Val Phe Phe Ala
1               5                   10                  15

Glu Asp Val Gly Ser Asn Lys Gly Ala Ile Ile Gly Leu Met Val Gly
            20                  25                  30

Gly

<210> SEQ ID NO 3
<211> LENGTH: 33
<212> TYPE: PRT
<213> ORGANISM: Homo Sapiens

<400> SEQUENCE: 3

Arg His Asp Ser Gly Tyr Glu Val His His Gln Lys Leu Val Phe Phe
1               5                   10                  15

Ala Glu Asp Val Gly Ser Asn Lys Gly Ala Ile Ile Gly Leu Met Val
            20                  25                  30

Gly

<210> SEQ ID NO 4
<211> LENGTH: 33
<212> TYPE: PRT
<213> ORGANISM: Homo Sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly

<210> SEQ ID NO 5
<211> LENGTH: 35
<212> TYPE: PRT
<213> ORGANISM: Homo Sapiens

<400> SEQUENCE: 5

His Asp Ser Gly Tyr Glu Val His His Gln Lys Leu Val Phe Phe Ala
1               5                   10                  15

Glu Asp Val Gly Ser Asn Lys Gly Ala Ile Ile Gly Leu Met Val Gly
            20                  25                  30

Gly Val Val
        35

<210> SEQ ID NO 6
<211> LENGTH: 36
<212> TYPE: PRT
<213> ORGANISM: Homo Sapiens

<400> SEQUENCE: 6

Arg His Asp Ser Gly Tyr Glu Val His His Gln Lys Leu Val Phe Phe
1               5                   10                  15

Ala Glu Asp Val Gly Ser Asn Lys Gly Ala Ile Ile Gly Leu Met Val
            20                  25                  30

Gly Gly Val Val
        35

<210> SEQ ID NO 7
<211> LENGTH: 35
<212> TYPE: PRT

<213> ORGANISM: Homo Sapiens

<400> SEQUENCE: 7

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met
        35

<210> SEQ ID NO 8
<211> LENGTH: 37
<212> TYPE: PRT
<213> ORGANISM: Homo Sapiens

<400> SEQUENCE: 8

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly
        35

<210> SEQ ID NO 9
<211> LENGTH: 38
<212> TYPE: PRT
<213> ORGANISM: Homo Sapiens

<400> SEQUENCE: 9

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly
        35

<210> SEQ ID NO 10
<211> LENGTH: 38
<212> TYPE: PRT
<213> ORGANISM: Homo Sapiens

<400> SEQUENCE: 10

Glu Phe Arg His Asp Ser Gly Tyr Glu Val His His Gln Lys Leu Val
1               5                   10                  15
Phe Phe Ala Glu Asp Val Gly Ser Asn Lys Gly Ala Ile Ile Gly Leu
            20                  25                  30
Met Val Gly Gly Val Val
        35

<210> SEQ ID NO 11
<211> LENGTH: 39
<212> TYPE: PRT
<213> ORGANISM: Homo Sapiens

<400> SEQUENCE: 11

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly Val

<210> SEQ ID NO 12
<211> LENGTH: 40
<212> TYPE: PRT
<213> ORGANISM: Homo Sapiens

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 13
<211> LENGTH: 40
<212> TYPE: PRT
<213> ORGANISM: Homo Sapiens

<400> SEQUENCE: 13

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 14
<211> LENGTH: 41
<212> TYPE: PRT
<213> ORGANISM: Homo Sapiens

<400> SEQUENCE: 14

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val
        35                  40

<210> SEQ ID NO 15
<211> LENGTH: 41
<212> TYPE: PRT
<213> ORGANISM: Homo Sapiens

<400> SEQUENCE: 15

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly
        35                  40

<210> SEQ ID NO 16
<211> LENGTH: 42
<212> TYPE: PRT
<213> ORGANISM: Homo Sapiens

<400> SEQUENCE: 16

Asp Ala Glu Phe Arg His Asp Ser Gly Tyr Glu Val His His Gln Lys

```
             1               5                  10                  15
Leu Val Phe Phe Ala Glu Asp Val Gly Ser Asn Lys Gly Ala Ile Ile
             20                  25                  30
Gly Leu Met Val Gly Gly Val Val Ile Ala
             35                  40

<210> SEQ ID NO 17
<211> LENGTH: 42
<212> TYPE: PRT
<213> ORGANISM: Homo Sapiens

<400> SEQUENCE: 17

Val Lys Met Asp Ala Glu Phe Arg His Asp Ser Gly Tyr Glu Val His
1               5                  10                  15
His Gln Lys Leu Val Phe Phe Ala Glu Asp Val Gly Ser Asn Lys Gly
             20                  25                  30
Ala Ile Ile Gly Leu Met Val Gly Gly Val
             35                  40

<210> SEQ ID NO 18
<211> LENGTH: 43
<212> TYPE: PRT
<213> ORGANISM: Homo Sapiens

<400> SEQUENCE: 18

Val Lys Met Asp Ala Glu Phe Arg His Asp Ser Gly Tyr Glu Val His
1               5                  10                  15
His Gln Lys Leu Val Phe Phe Ala Glu Asp Val Gly Ser Asn Lys Gly
             20                  25                  30
Ala Ile Ile Gly Leu Met Val Gly Gly Val Val
             35                  40

<210> SEQ ID NO 19
<211> LENGTH: 44
<212> TYPE: PRT
<213> ORGANISM: Homo Sapiens

<400> SEQUENCE: 19

Ile Ser Glu Val Lys Met Asp Ala Glu Phe Arg His Asp Ser Gly Tyr
1               5                  10                  15
Glu Val His His Gln Lys Leu Val Phe Phe Ala Glu Asp Val Gly Ser
             20                  25                  30
Asn Lys Gly Ala Ile Ile Gly Leu Met Val Gly Gly
             35                  40

<210> SEQ ID NO 20
<211> LENGTH: 46
<212> TYPE: PRT
<213> ORGANISM: Homo Sapiens

<400> SEQUENCE: 20

Ile Ser Glu Val Lys Met Asp Ala Glu Phe Arg His Asp Ser Gly Tyr
1               5                  10                  15
Glu Val His His Gln Lys Leu Val Phe Phe Ala Glu Asp Val Gly Ser
             20                  25                  30
Asn Lys Gly Ala Ile Ile Gly Leu Met Val Gly Gly Val Val
             35                  40                  45

<210> SEQ ID NO 21
<211> LENGTH: 48
```

```
<212> TYPE: PRT
<213> ORGANISM: Homo Sapiens

<400> SEQUENCE: 21

Glu Glu Ile Ser Glu Val Lys Met Asp Ala Glu Phe Arg His Asp Ser
1               5                   10                  15

Gly Tyr Glu Val His His Gln Lys Leu Val Phe Phe Ala Glu Asp Val
            20                  25                  30

Gly Ser Asn Lys Gly Ala Ile Ile Gly Leu Met Val Gly Gly Val Val
        35                  40                  45

<210> SEQ ID NO 22
<211> LENGTH: 49
<212> TYPE: PRT
<213> ORGANISM: Homo Sapiens

<400> SEQUENCE: 22

Thr Glu Glu Ile Ser Glu Val Lys Met Asp Ala Glu Phe Arg His Asp
1               5                   10                  15

Ser Gly Tyr Glu Val His His Gln Lys Leu Val Phe Phe Ala Glu Asp
            20                  25                  30

Val Gly Ser Asn Lys Gly Ala Ile Ile Gly Leu Met Val Gly Gly Val
        35                  40                  45

Val
```

MEASUREMENT METHOD FOR AMYLOID PRECURSOR PROTEIN CLEAVAGE PEPTIDES

The instant application contains a Sequence Listing which has been submitted in ASCII format via EFS-WEB and is hereby incorporated by reference in its entirety. Said ASCII copy created on Jul. 13, 2016, is named sequence.txt and is 8,530 bytes.

TECHNICAL FIELD

The present invention pertains to the neuroscience basic research field and the clinical medicine field, and relates to a measurement method for amyloid precursor protein (APP) cleavage peptides including amyloid beta (Aβ) peptides that are considered to be deeply involved in development of Alzheimer's disease.

BACKGROUND ART

Alzheimer's disease (AD) is a principal cause of dementia, and occupies 50 to 60% of the entire dementia. The number of patients suffering from dementia was more than or equal to 24 million in the world in 2001, and is estimated to reach 81 million in 2040 (Non-Patent Document 1). It is considered that amyloid beta (Aβ) peptides are deeply involved in development of Alzheimer's disease. Aβ peptides are produced as a result of proteolysis of amyloid precursor protein (APP) which is a single-pass transmembrane protein composed of 770 amino acid residues, by β-secretase and γ-secretase (see FIG. 1). Appearance of senile plaques due to aggregation of Aβ peptides accompanying fibrosis triggers aggregation and accumulation of tau protein inside neurocytes to cause nerve malfunction and neuronal cell death. It is considered that this results in extreme deterioration of the cognitive ability. It has long been known that Aβ peptides mainly consists of 40 mer (Aβ1-40) and 42 mer (Aβ1-42) and migrate into cerebrospinal fluid (CSF) and blood. Further, in recent years, existence of amyloid beta peptides having lengths different from those of Aβ1-40 and Aβ1-42 in CSF has been reported (Non-Patent Document 2).

Alzheimer's disease develops latently and advances slowly. Diagnosis of Alzheimer's disease is made by conducting ADAS-cog, MMSE, DemTect, SKT, or a test of cognitive function such as a clock drawing test for examining the clinical symptom, and examination of image findings of magnetic resonance imaging diagnosis (MRI), positron emission tomography (PET) and the like in combination. While MRI is an image diagnostic method capable of detecting cerebral degenerative atrophy, unfortunately, cerebral atrophy is not specific for Alzheimer's disease. Meanwhile, as an image diagnostic method that visualizes accumulation of detected molecules on amyloid deposits (PIB: Pittsburgh compound-B), PIB-PET has been known. It has been found that thioflavin T-analogue (11C) PIB gradually accumulates in a specific region of the brain of a patient suffering from MCI or mild Alzheimer's disease, and hence PIB-PET is an optimum tool as a method for detecting amyloid deposits. From the findings of AD necropsy brain, it is found that a large quantity of senile plaques has already accumulated even in cases of mild cognitive function decline. This leads the current inference that aggregation and deposition of Aβ peptides start quite long before exteriorization of clinical symptoms such as amnesia, and the result supporting this inference is reported also in the findings of PIB-PET.

A biomarker existing in blood or cerebrospinal fluid (CSF) is an effective method capable of detecting the development and progression of a disease on the molecular level. In Alzheimer's disease, a decrease in concentration of Aβ1-42 in CSF or concentration ratio of Aβ1-42/Aβ1-40, and an increase in total tau value or phosphorylation tau value are reported to be a useful diagnostic marker (Patent Document 1: JP-A-2010-19864, Non-Patent Document 3). However, there is little opportunity to collect CSF from a patient not developing a symptom of dementia for diagnose.

Under these circumstances, the potentiality of Aβ1-42 existing in blood as an AD diagnostic marker is expected in a blood examination; however, it has been reported that the relationship between blood Aβ1-42 concentration and AD development is low unlike the case of CSF Aβ1-42 (Non-Patent Document 3). The reason for this has not been elucidated yet.

Also, Patent Document 2: JP-A-2013-63976 discloses a monoclonal antibody that does not recognize a soluble Aβ monomer, but specifically binds only to a soluble Aβ oligomer, and also discloses a diagnostic method of Alzheimer's disease using the antibody. The paragraph [0104] of the publication discloses a method in which when the ratio of Aβ oligomer to Aβ monomer in a sample of a subject is higher than that of a normal healthy person, the subject is determined as being a candidate for Alzheimer's disease.

Non-Patent Document 4 discloses production of 6E10/4G8 F(ab')-(PEG)$_{24}$ beads using F(ab') prepared from two kinds of anti-Aβ antibodies (clones 6E10 and 4G8), and also discloses that the detection sensitivity of human plasma peptides by a mass spectrometer is improved by immunoprecipitation (IP) using the beads (Non-Patent Document 4).

PRIOR ART DOCUMENTS

Patent Documents

Patent Document 1: JP-A-2010-19864
Patent Document 2: JP-A-2013-63976

Non-Patent Documents

Non-Patent Document 1: Blennow K, de Leon M J, Zetterberg H.: Alzheimer's disease. Lancet. 2006 Jul. 29; 368 (9533): 387-403
Non-Patent Document 2: Portelius E, Westman-BrinkmalmA, Zetterberg H, Blennow K.: Determination of beta-amyloid peptide signatures in cerebrospinal fluid using immunoprecipitation-mass spectrometry. J Proteome Res. 2006 April; 5(4): 1010-6
Non-Patent Document 3: Hampel H, Shen Y, Walsh D M, Aisen P, Shaw L M, Zetterberg H, Trojanowski J Q, Blennow K.: Biological markers of amyloid beta-related mechanisms in Alzheimer's disease. Exp Neurol. 2010 June; 223(2): 334-46
Non-Patent Document 4: Kaneko N, Yoshimori T, Yamamoto R, Capon D J, Shimada T, Sato T A, Tanaka K.: Multi epitope-targeting immunoprecipitation using F(ab') fragments with high affinity and specificity for the enhanced detection of a peptide with matrix-assisted laser desorption ionization-time-of-flight mass spectrometry. Anal Chem. 2013 Mar. 19; 85(6): 3152-9

SUMMARY OF THE INVENTION

Problems to be Solved by the Invention

It has been found that a large quantity of amyloid has been deposited before exteriorization of the cognitive function decline in an Alzheimer's disease (AD) patient. However, in the current technology, there is no method capable of detecting a patient at the starting point of the aggregation and deposition of Aβ peptides. Even in the case of diagnosis with PIB-PET that is effective for detecting amyloid accumulation, there is extremely little opportunity for a potential AD patient in which the cognitive function decline is not exteriorized to undergo PIB-PET. Therefore, a simplified early stage diagnostic method capable of detecting amyloid formation before exteriorization of clinical symptoms has been demanded.

As described above, a biomarker existing in blood or cerebrospinal fluid (CSF) is an effective method capable of detecting the development and progression of a disease on the molecular level. Patent Document 1 and Non-Patent Document 3 described above have reported that in Alzheimer's disease, a decrease in concentration of Aβ1-42 in CSF or concentration ratio of Aβ1-42/Aβ1-40, and an increase in total tau value or phosphorylation tau value are reported to be a useful diagnostic marker. On the other hand, however, Non-Patent Document 3 has reported that the relationship between blood Aβ1-42 concentration and AD development is low unlike the case of CSF Aβ1-42.

In previous reports regarding amyloid beta (Aβ) in blood, the correlativity with AD is examined only for concentrations of two kinds Aβ1-40 and Aβ1-42 in blood. However, existence of shorter Aβ peptides that are cleaved on the N-terminal side or C-terminal side of Aβ1-40 in CSF have been found besides Aβ1-40 and Aβ1-42 by a combinational method of immunoprecipitation and a mass spectrometer. This leads to the inference that cleavage Aβ peptides other than Aβ1-40 and Aβ1-42 also exist in blood, and these can possibly be used as a marker for AD diagnosis. However, in blood, it is technically difficult to detect Aβ peptides that are present in a smaller quantity than in CSF by immunoprecipitation and a mass spectrometer, and no successful case has been known heretofore.

Non-Patent Document 4 described above discloses that the detection sensitivity in the mass spectrometer is improved by using 6E10/4G8 F(ab')-(PEG)$_{24}$ beads containing two kinds of anti-Aβ antibodies (clones 6E10 and 4G8), as results of conducting immunoprecipitation (IP) for synthetic peptides spiked to human plasma with use of the 6E10/4G8 F(ab')-(PEG)$_{24}$ beads and evaluating the sensitivity of mass spectrometry (MS). Also disclosed is detection of plasma endogenous Aβ1-40 peptide by a mass spectrometer from 250 µL of a human plasma sample.

However, in Non-Patent Document 4 describe above, the signal of Aβ1-40 peptide detectable by the mass spectrometer was low, and the S/N ratio was 4.1. This S/N ratio of 4.1 is a S/N ratio close to the detection limit (S/N=3). If the plasma Aβ1-40 peptide concentration is much low in a specimen that is different from the specimen used in Non-Patent Document 4 above, the Aβ1-40 peptide concentration may be less than or equal to the detection limit. If clinical samples of many specimens are measured, there is a risk that an Aβ1-40 peptide cannot be detected in many specimens. Although the signal may be raised by conducting immunoprecipitation and mass spectrometry for a larger amount of sample, the amount of a clinical sample actually collected by blood collection from a patient is limited. Therefore, in consideration of the amount of blood collection from a patient for measuring the clinical sample, the amount to be analyzed is preferably less than or equal to 1000 µL.

An object of the present invention is to provide a measurement method for amyloid precursor protein (APP) cleavage peptides including amyloid beta (Aβ) peptides that are considered as being deeply involved in development of Alzheimer's disease. In particular, the object of the present invention is to provide a measurement method capable of detecting amyloid precursor protein (APP) cleavage peptides even when an amount of a blood sample is small, and/or when the peptides are present in a trace amount in the blood sample.

Means for Solving the Problems

As a result of diligent efforts, the present inventor has succeeded in detecting APP cleavage peptides including Aβ1-40 and Aβ1-42 in human plasma even when an amount of a blood sample is small, and/or when the peptides are present in a trace amount in the blood sample, and accomplished the present invention. Further, eight kinds of novel APP cleavage peptides have been found from the detected 22 kinds of APP cleavage peptides.

The present invention includes the following aspects.
(1) A method for measuring amyloid precursor protein (APP) cleavage peptides in a blood sample, the method comprising the steps of:

bringing a blood sample into contact with an antibody-immobilizing carrier in a binding solution to bind the antibody-immobilizing carrier and APP cleavage peptides contained in the blood sample, the antibody-immobilizing carrier including a carrier, and an antibody bound to the carrier and selected from the group consisting of an immunoglobulin having an antigen binding site capable of recognizing amyloid precursor protein (APP) cleavage peptides and an immunoglobulin fragment containing an antigen binding site capable of recognizing amyloid precursor protein (APP) cleavage peptides;

washing a bound body of the antibody-immobilizing carrier and the APP cleavage peptides using a washing solution;

dissociating the APP cleavage peptides from the antibody-immobilizing carrier using an acidic aqueous solution containing an organic solvent; and detecting the dissociated APP cleavage peptides.

Here, the APP cleavage peptides refer to cleaved (truncated) peptides obtained by proteolysis of amyloid precursor protein (APP) consisting of 770 amino acid residues. Typically, referring to FIG. 1, the APP cleavage peptides are produced by proteolysis of amyloid precursor protein (APP) by β-secretase and γ-secretase. However, the present invention has revealed that a variety of APP cleavage peptides having different cleavage sites exist. The APP cleavage peptides also include known amyloid beta (Aβ) peptides.
(2) The method according to (1), wherein in the dissociating step, the acidic aqueous solution containing an organic solvent has an organic solvent concentration of more than 20% (v/v).
(3) The method according to (1) or (2), wherein in the binding step, the binding solution is a neutral buffer containing a surfactant.
(4) The method according to (3), wherein the neutral buffer has a surfactant concentration of 0.001 to 10% (v/v).
(5) The method according to (3) or (4), wherein the surfactant is selected from the group consisting of a neutral surfactant having maltose in a hydrophilic part, a neutral surfactant having trehalose in a hydrophilic part, and a neutral surfactant having glucose in a hydrophilic part.
(6) The method according to any of (1) to (5), wherein in the washing step, washing is conducted by using a neutral buffer containing a surfactant as the washing solution, and then washing is conducted by using an aqueous solution containing ammonium ions as the washing solution.
(7) The method according to any of (1) to (6), wherein in the detecting step, detection by mass spectrometry is conducted.
(8) The method according to (7), wherein in the mass spectrometry, a matrix-assisted laser desorption/ionization mass spectrometer is used.
(9) The method according to (8), wherein in the matrix-assisted laser desorption/ionization mass spectrometer, a matrix in a concentration of 0.1 to 20 mg/mL, and a matrix additive in a concentration of 0.1 to 10% (w/v) are used.

Effects of the Invention

According to the present invention, it is possible to detect APP cleavage peptides including Aβ1-40 and Aβ1-42 in a blood sample even when an amount of the blood sample is small, and/or when the peptides are present in a trace amount in the blood sample. Further, the present invention has found eight novel APP cleavage peptides. These eight novel APP cleavage peptides have not been found even in cerebrospinal fluid (CSF).

The measurement method of the present invention can be used for early diagnosis (as a primary screening prior to PIB-PET), follow-up, and sensitivity evaluation tool for therapeutic agents (anti-amyloid beta antibody pharmaceuticals, β- and γ-secretase modulators etc.) of Alzheimer's disease; a tool for analyzing a amyloid precursor protein (APP) cleavage mechanism in basic research fields regarding development of Alzheimer's disease.

BRIEF DESCRIPTION OF DRAWINGS

FIG. 3(B) shows a mass spectrum when a washing step with an ammonium acetate buffer (pH 7.4) is added, and FIG. 3(A) shows a mass spectrum when the washing step with an ammonium acetate buffer (pH 7.4) is not added.

FIG. 6(A) shows a mass spectrum obtained by conducting an elution operation using 2.5 μL of 70% (v/v) acetonitrile containing 5 mM hydrochloric acid with respect to 150 μg of 6E10/4G8 F(ab')-immobilizing beads, FIG. 6(B) shows a mass spectrum when IP-MS is conducted by using 150 μg of Cysteine-$PEG_{24}$ beads with respect to 250 μL of a human plasma sample, and FIG. 6(C) shows a mass spectrum when IP-MS is conducted by using 150 μg of 6E10/4G8 F(ab')-immobilizing beads with respect to 250 μL of a human plasma sample.

FIG. 7 shows mass spectra in Example 6, and FIGS. 7(A) to (E) each show mass spectra when the following binding solution and washing solution are used. (A) binding solution (1% (w/v) OTG, 800 mM GlcNAc, 100 mM Tris-HCl, 300 mM NaCl, pH 7.4), washing solution (0.5% (w/v) OTG, 50 mM Tris-HCl, 150 mM NaCl, pH 7.4) (B) binding solution (3% (w/v) OG, 800 mM GlcNAc, 100 mM Tris-HCl, 300 mM NaCl, pH 7.4), washing solution (1.5% (w/v) OG, 50 mM Tris-HCl, 150 mM NaCl, pH 7.4) (C) binding solution (0.3% (w/v) DM, 800 mM GlcNAc, 100 mM Tris-HCl, 300 mM NaCl, pH 7.4), washing solution (0.15% (w/v) DM, 50 mM Tris-HCl, 150 mM NaCl, pH 7.4) (D) binding solution (0.03% (w/v) DDM, 800 mM GlcNAc, 100 mM Tris-HCl, 300 mM NaCl, pH 7.4), washing solution (0.015% (w/v) DDM, 50 mM Tris-HCl, 150 mM NaCl, pH 7.4) (E) binding solution (0.4% (w/v) NTM, 800 mM GlcNAc, 100 mM Tris-HCl, 300 mM NaCl, pH 7.4), washing solution (0.2% (w/v) NTM, 50 mM Tris-HCl, 150 mM NaCl, pH 7.4)

FIG. 12 shows MALDI spectra of APP cleavage peptides purified by immunoprecipitation from human plasma using 6E10/4G8 F(ab')-immobilizing beads in Example 8. FIG.

12(A) shows a mass spectrum of Linear TOF, and FIG. 12(B) shows a mass spectrum of QIT reflectron TOF. The horizontal axis indicates m/z, and the vertical axis indicates relative intensity of ion.

FIG. 13 shows mass spectra of MS/MS analysis regarding molecular weight-related ion peaks of 20 kinds of the APP cleavage peptides detected by MS in Experimental Example 1. FIGS. 13(A) and (B) show mass spectra of MS/MS analysis for each of APP cleavage peptides.

FIG. 14 is a continuation of FIG. 13, and FIGS. 14(C) and (D) show mass spectra of MS/MS analysis for each of APP cleavage peptides.

FIG. 15 is a continuation of FIG. 14, and FIGS. 15(E) and (F) show mass spectra of MS/MS analysis for each of APP cleavage peptides.

FIG. 16 is a continuation of FIG. 15, and FIGS. 16(G) and (H) show mass spectra of MS/MS analysis for each of APP cleavage peptides.

FIG. 17 is a continuation of FIG. 16, and FIGS. 17(I) and (J) show mass spectra of MS/MS analysis for each of APP cleavage peptides.

FIG. 18 is a continuation of FIG. 17, and FIGS. 18(K) and (L) show mass spectra of MS/MS analysis for each of APP cleavage peptides.

FIG. 19 is a continuation of FIG. 18, and FIGS. 19(M) and (N) show mass spectra of MS/MS analysis for each of APP cleavage peptides.

FIG. 20 is a continuation of FIG. 19, and FIGS. 20(O) and (P) show mass spectra of MS/MS analysis for each of APP cleavage peptides.

FIG. 21 is a continuation of FIG. 20, and FIGS. 21(Q) and (R) show mass spectra of MS/MS analysis for each of APP cleavage peptides.

FIG. 22 is a continuation of FIG. 21, and FIGS. 22(S) and (T) show mass spectra of MS/MS analysis for each of APP cleavage peptides.

MODES FOR CARRYING OUT THE INVENTION

Figure 1:
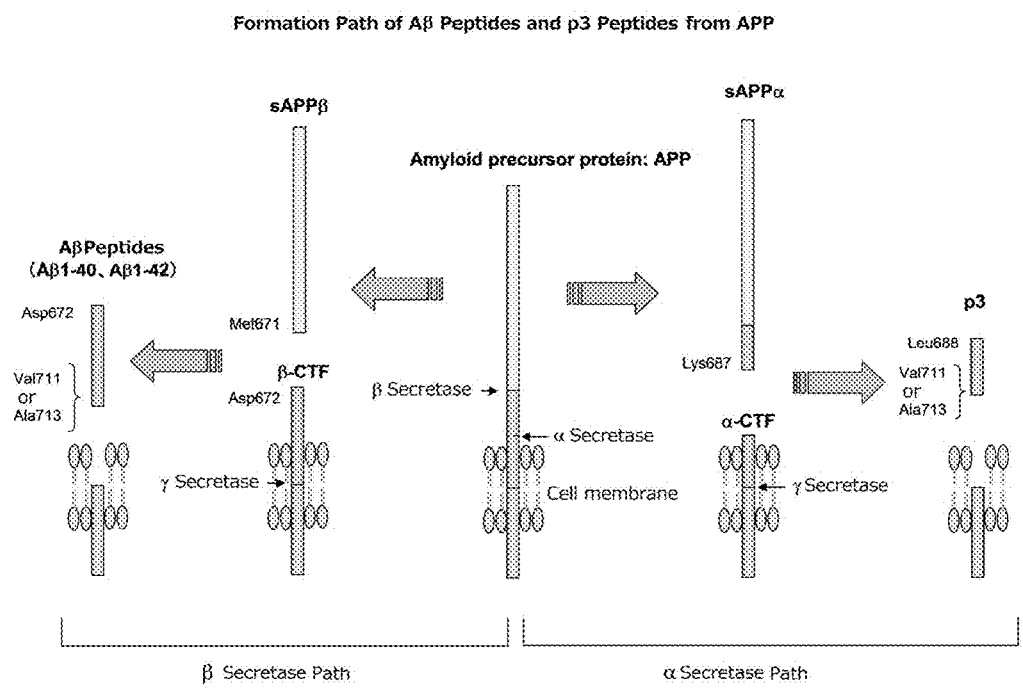
FIG. 1 shows a diagram schematically showing the generation route of Aβ peptides and p3 peptides by lysis of amyloid precursor protein (APP).

The method of the present invention is a method for measuring amyloid precursor protein (APP) cleavage peptides in a blood sample, and comprises:

bringing a blood sample into contact with an antibody-immobilizing carrier that includes a carrier and an antibody bound to the carrier, in a binding solution to bind the antibody-immobilizing carrier and APP cleavage peptides contained in the blood sample;

washing a bound body of the antibody-immobilizing carrier and the APP cleavage peptides using a washing solution;

dissociating the APP cleavage peptides from the antibody-immobilizing carrier using an acidic aqueous solution containing an organic solvent; and detecting the dissociated APP cleavage peptides.

[1. Antibody-Immobilizing Carrier]

The antibody-immobilizing carrier used in the present invention consists of a carrier, and an immunoglobulin having an antigen binding site capable of recognizing amyloid precursor protein (APP) cleavage peptides and/or an immunoglobulin fragment containing an antigen binding site capable of recognizing amyloid precursor protein (APP) cleavage peptides bound to the carrier. Examples of the immunoglobulin include IgG, IgM, IgA, IgY, IgD, and IgE. Examples of IgG include IgG1, IgG2, IgG3, IgG4, and the like. Examples of the immunoglobulin (hereinafter, also referred to as "anti-APP cleavage peptides antibody") having an antigen binding site capable of recognizing amyloid precursor protein (APP) cleavage peptides include 6E10, 4G8, 1E11, 11A50-B10, 12F4, 9C4, 82E1, 12B2, 1A10, and the like. These antibodies are known as anti-amyloid beta antibodies. The immunoglobulin fragment containing an antigen binding site capable of recognizing amyloid precursor protein (APP) cleavage peptides can be selected from the group consisting of F(ab')$_2$, F(ab'), F(ab), Fd, Fv, L chain, and H chain. Among these, the immunoglobulin fragment is preferably selected from the group consisting of an immunoglobulin F(ab') fragment, an immunoglobulin F(ab) fragment, and a Fv fragment not having a Fc region from the viewpoint of suppressing non-specific adsorption. The anti-APP cleavage peptide antibody to be immobilized to the carrier may be a monoclonal antibody or a polyclonal antibody. The antibody-immobilizing carrier used in the present invention can be an antibody-immobilizing carrier in which the above anti-APP cleavage peptide antibody and/or anti-APP cleavage peptide antibody fragment is immobilized to a carrier by an appropriate method.

The material of the carrier used herein may be a known material, and for example, may be selected from the group consisting of agarose, sepharose, dextran, silica gel, polyacrylamide, polystyrene, polyethylene, polypropylene, polyester, polyacrylonitrile, (meth)acrylic acid polymer, fluororesin, metal complex resin, glass, metal, and a magnetic substance.

The carrier may have any shape including a planar shape, a globular shape and other shapes. For example, the carrier may be a chip, or beads or may form a flow channel wall inside a micro device used for separation and/or concentration of a target substance. The carrier surface has a bonding functional group.

The antibody may be bound to the carrier via a spacer. Examples of the spacer include high molecular weight polymers. More specifically, the spacer may contain an oxyalkylene group. An oxyalkylene group-containing group is a bivalent group, and may be, for example, a C2 to C6 oxyalkylene group-containing group. More specifically, oxyalkylene in an oxyalkylene group-containing group is ethylene oxide or propylene oxide. The oxyalkylene group-containing group is preferably an organic high molecular weight polymer, namely a polyoxyalkylene group-containing group. The polyoxyalkylene group-containing group is preferably a polyalkylene glycol group generated by polymerization (for example, degree of polymerization is 2 to 40) of C2 to C6 alkylene glycol. For example, the polyoxyalkylene group-containing group can be selected from the group consisting of a polyethylene glycol group (group generated by polymerization of ethylene glycol) and a polypropylene glycol group (group generated by polymerization of 1,2-propanediol or 1,3-propanediol).

For example, the spacer may be an organic high molecular weight polymer selected from the group consisting of polyoxyalkylated polyol, polyvinyl alcohol, polyvinyl alkyl ether, polysaccharide, biodegradable polymer, and lipid polymer. The alkyl group in the polyoxyalkylated polyol and the polyvinyl alkyl ether may be, for example, a C1 to C6 alkyl group, preferably a C1 to C3 alkyl group. Examples of the polysaccharide include dextran, mucopolysaccharide, and chitins. An example of the mucopolysaccharide includes hyaluronic acid. Examples of the biodegradable polymer include PLA (poly(lactic acid)) and PLGA (poly(lactic-glycolic acid)).

The spacer in the present invention may be those containing one kind of the above examples, or may be those containing two or more kinds arbitrarily selected from the above examples. The spacer may be linear or branched.

The antibody-immobilizing carrier used in the present invention can be prepared by binding a carrier, and an antibody, and a spacer substance if used, via respective boding functional groups such as a covalently bonding functional group, an ionic-bonding functional group, and a hydrogen bonding functional group possessed by these elements by a known method depending on the kinds of the functional groups.

[2. Binding Step]

First, a blood sample is brought into contact with the antibody-immobilizing carrier in a binding solution, to bind the antibody-immobilizing carrier and APP cleavage peptides contained in the blood sample.

The blood sample includes whole blood, plasma, serum and the like. The blood sample can be prepared by appropriately treating whole blood collected from an individual. The treatment conducted in the case of preparing a blood sample from collected whole blood is not particularly limited, and any treatment that is clinically acceptable may be conducted. For example, centrifugal separation or the like may be conducted. The blood sample subjected to the binding step may be appropriately stored at low temperature by freezing in the intermediate stage of the preparation step or in the post stage of the preparation step. In the present invention, the blood sample is disposed of rather than being returned to the individual from which the blood sample is derived. The use of a blood sample as a subject sample is preferable in that collection of a sample is minimally invasive when the sample is solid or cerebrospinal fluid, and that a blood sample is a subject sample for screening of Alzheimer's disease or other diseases in a general medical examination, a thorough physical examination and the like.

As the binding solution, a binding solution that is used in ordinary immunoprecipitation (IP) can be used. The composition of the binding solution preferably includes a surfactant for suppressing non-specific adsorption. As the surfactant, preferred is a neutral surfactant that is less likely to cause denaturation of protein such as antibody, is easily removed in the washing step, and does not suppress a signal of APP cleavage peptides even if the surfactant is contaminated in mass spectrometry when the mass spectrometry is employed in the subsequent detecting step. Specific examples of the surfactant include a neutral surfactant having maltose in a hydrophilic part, a neutral surfactant having trehalose in a hydrophilic part, and a neutral surfactant having glucose in a hydrophilic part. The hydrophobic part of such a neutral surfactant is, but not particularly limited to, preferably an about C7 to C14 alkyl group. The binding solution is preferably a neutral buffer containing the surfactant selected from the above-mentioned surfactants.

Examples of the neutral surfactant having maltose in a hydrophilic part include:
n-Decyl-β-D-maltoside (DM) [cmc: 0.087%]
n-Dodecyl-β-D-maltoside (DDM) [cmc: 0.009%]
n-Nonyl-β-D-thiomaltoside (NTM) [cmc: 0.116%], and the like. The "cmc" represents critical micelle concentration.

Examples of the neutral surfactant having trehalose in a hydrophilic part include:
α-D-Glucopyranosyl-α-Dglucopyranoside monooctanoate (Trehalose C8) [cmc: 0.262%]
α-D-Glucopyranosyl-α-Dglucopyranoside monododecanoate (Trehalose C12) [cmc: 0.008%]
α-D-Glucopyranosyl-α-Dglucopyranoside monomyristate (Trehalose C14) [cmc: 0.0007%], and the like.

Examples of the neutral surfactant having glucose in a hydrophilic part include:
n-Octyl-β-D-thioglucoside (OTG) [cmc: 0.278%]
n-Octyl-β-D-glucoside (OG) [cmc: 0.731%]
n-Heptyl-β-D-thioglucoside (HTG) [cmc: 0.883%], and the like.

One or a combination of two or more of the aforementioned neutral surfactants can be used. Among these, the neutral surfactant having maltose in a hydrophilic part is preferred, and a combination of n-Dodecyl-β-D-maltoside (DDM) and n-Nonyl-β-D-thiomaltoside (NTM) is preferable because when mass spectrometry is employed in the subsequent detecting step, a strong signal of APP cleavage peptides can be obtained while a signal of the substance non-specifically adsorbed to the antibody-immobilizing carrier is reduced in the mass spectrometry.

The neutral buffer as the binding solution has a surfactant concentration of, for example, 0.001 to 10% (v/v), preferably 0.01 to 5% (v/v), more preferably 0.05 to 2% (v/v), although the surfactant concentration is not particularly limited. By employing such a surfactant concentration, binding reaction between the antibody and the target APP cleavage peptides to be bound is likely to occur satisfactorily. The neutrality of the neutral buffer means about pH 6.5 to 8.5. Examples of the buffer composition include a Tris buffer, a phosphate buffer, a HEPES buffer, and the like.

Further, prior to the binding step, a blood sample is preferably subjected to a pretreatment. In the pretreatment, for example, antibodies such as IgG and IgM contained in the blood sample are removed. The blood sample contains antibodies derived from the sample that bind with the antibody immobilized to the carrier for use in the binding step. Therefore, by removing the antibodies derived from the sample prior to the binding step, it is possible to prevent the antibodies derived from the sample from binding with the antibody used in the binding step. The antibodies derived from the sample can be removed by bringing the blood sample into contact with carriers to which Protein G, Protein A, Protein L, an anti-IgG antibody, an anti-IgM antibody, an anti-IgA antibody, an anti-IgY antibody, an anti-IgD antibody, an anti-IgE antibody and the like are bound.

[3. Washing Step]

Next, a bound body of the antibody-immobilizing carrier and the APP cleavage peptides obtained by the binding step is washed with the use of a washing solution.

In the washing step, it is preferred that first, washing is conducted by using a neutral buffer containing a surfactant as the washing solution, and then washing is conducted by using an aqueous solution containing ammonium ions as the washing solution.

As the neutral buffer containing a surfactant as the washing solution, those similar to the neutral buffer containing a surfactant as the binding solution described above can be used. First, by conducting washing with the use of the neutral buffer containing a surfactant, unnecessary components such as highly hydrophobic blood protein, lipid, and glycolipid are ordinarily removed. Regarding the neutrality of the neutral buffer, pH close to that of the body fluid is suited for an antigen-antibody binding reaction, and for example, pH 6.5 to 8.5 is preferred, and pH 7.0 to 8.0 is more preferred.

Then, washing is preferably conducted by using an aqueous solution containing ammonium ions. By conducting washing with the use of an aqueous solution containing ammonium ions, it is possible to efficiently remove a cationic metal contained in the neutral buffer containing a surfactant remaining on the surface of the antibody-immobilizing carrier. While a cationic metal causes ion suppression when mass spectrometry is employed in the subsequent detecting step, an ammonium ion is less likely to cause ion suppression because it is a highly volatile substance. This contributes to improvement in sensitivity of analysis (improvement in S/N ratio) of the bound target APP cleavage peptides.

Examples of the aqueous solution containing ammonium ions include an ammonium acetate buffer, an ammonium carbonate buffer, and the like. The concentration of ammonium ion is not particularly limited, and may be for example, about 5 to 1,000 mM, and also may be about 50 to 200 mM. It can be appropriately determined depending on the configuration of the antibody-immobilizing carrier. Further, washing with an aqueous solution containing ammonium ions can be followed by washing with water.

In the washing step, by subjecting the carrier surface to a fluid pressure of 0.01 to 500 MPa, preferably 0.05 to 300 MPa, more preferably 0.1 to 200 MPa of the washing solution, unnecessary components can be removed. If the fluid pressure is below the aforementioned range, a desired washing effect tends not to be obtained. If the fluid pressure exceeds the aforementioned range, the binding between the antibody and the bound target APP cleavage peptides may be cleaved. By conducting the washing in a higher pressure condition, it is possible to improve the efficiency of removing non-specific adsorbed substance on the antibody-immobilizing carrier, and this contributes to improvement in sensitivity of analysis (improvement in S/N ratio) of the bound target APP cleavage peptides.

A specific technique for washing is not particularly limited. For example, in the case of a globular carrier, it can be washed by stirring in a washing liquid. In the case of a planar carrier, it can be washed by spraying a high-pressure washing liquid from a washing nozzle. More specifically, in order to wash a specific region on the planar carrier under high pressure, a washing nozzle having an inner diameter suited for the area of the region can be used. This nozzle is formed of, for example, a double tube in which the inner tube can be functioned exclusively for water injection for spraying the washing liquid onto the carrier surface, and the outer tube can be functioned exclusively for water ejection for sucking the washing liquid sprayed on the carrier surface.

[4. Dissociating Step]

Next, for the bound body of the antibody-immobilizing carrier and the APP cleavage peptides after washing, the APP cleavage peptides are dissociated from the antibody-immobilizing carrier by using an acidic aqueous solution containing an organic solvent as an eluent.

In order to dissociate an antigen from an antibody to which the antigen is bound (antigen-antibody composite), an acidic aqueous solution is generally brought into contact with the antigen-antibody composite. In the present invention, the APP cleavage peptides are dissociated from the antibody-immobilizing carrier to which the APP cleavage peptides are bound, and eluted by using an acidic aqueous solution containing an organic solvent. Examples of the organic solvent used in this case include organic solvents that mingle with water at an arbitrary ratio, such as acetonitrile, acetone, methanol, ethanol, isopropanol, chloroform and the like. While the concentration of the organic solvent in the acidic aqueous solution is not particularly limited, it is for example about 10 to 90% (v/v), preferably 20 to 80% (v/v), and more preferably about 25 to 70% (v/v). When the concentration of the organic solvent in the acidic aqueous solution falls within the aforementioned range, dissociation of the APP cleavage peptides from the carrier occurs efficiently. This contributes to improvement in sensitivity of analysis (improvement in S/N ratio) of the bound target APP cleavage peptides. If the concentration of the organic solvent is less than 10% (v/v), the effect of the organic solvent is not obtained, and the efficiency of dissociation of the APP cleavage peptides is not excellent. On the other hand, when the concentration of the organic solvent is more than 90% (v/v), the effect of the organic solvent is sufficiently obtained, and the efficiency of dissociation of the APP cleavage peptides is improved. For example, by using an aqueous solution containing 70% (v/v) acetonitrile in 5 mM acetic acid, a higher elution efficiency is easily obtained. The acidity of the acidic aqueous solution means about pH 1 to 3.5.

Normally, the acidic aqueous solution containing the organic solvent used for dissociation can be used also as an eluent to elute the APP cleavage peptides dissociated from the carrier. Alternatively, a person skilled in the art can appropriately select the eluent.

In the dissociating step, by bringing the carrier surface into contact with the eluent, the APP cleavage peptides can be dissociated and eluted. The carrier may be stirred in the eluent as is necessary.

[5. Detecting Step]

Next, the APP cleavage peptides that are dissociated and eluted are detected by an appropriate detecting system.

In the present invention, as examples of detecting systems, radioactivity measurement, enzyme activity measurement, fluorescence intensity measurement, and emission intensity measurement can be employed. For example, any solid-phase immunoassay method may be selected as a detecting system. For example, radio immunoassay (RIA), enzyme immunoassay (EIA, ELISA), fluorescence immunoassay (FIA), chemiluminescence immunoassay (CLIA) or the like is selected as a detecting system. A person skilled in the art can appropriately bind a label suited for such a detecting system (selected from the group consisting of a radioactive isotope, an enzyme, a fluorescent substance and a chemiluminescence substance) to the antibody.

In the present invention, as examples of detecting systems other than the aforementioned detecting systems, optical detecting systems such as surface plasmon resonance (SPR), sum-frequency generation (SFG), local plasmon resonance (LPR), ellipsometry and the like can be preferably employed. In the case of employing such an optical detecting system, a label is not required unlike the case of the aforementioned detecting systems.

In the present invention, as a further example other than the aforementioned detecting systems, mass spectrometry is also preferably employed. The mass spectrometry employed in this case is preferably mass spectrometry such as matrix-assisted laser desorption/ionization (MALDI) mass spectrometry or electrospray ionization (ESI) mass spectrometry. For example, a MALDI-TOF (matrix-assisted laser desorption/ionization-time of flight) mass spectrometer, a MALDI-IT (matrix-assisted laser desorption/ionization-ion trap) mass spectrometer, a MALDI-IT-TOF (matrix-assisted laser desorption/ionization-ion trap-time of flight) mass spectrometer, a MALDI-FTICR (matrix-assisted laser desorption/ionization-Fourier transformation ion cyclotron resonance) mass spectrometer, an ESI-QqQ (electrospray ionization-triple quadrupole) mass spectrometer, an ESI-Qq-TOF (electrospray ionization-tandem quadrupole-time of flight) mass spectrometer, an ESI-FTICR (electrospray ionization-Fourier transformation ion cyclotron resonance) mass spectrometer or the like can be employed.

A matrix and a matrix solvent can be appropriately determined by a person skilled in the art depending on the analysis subject (APP cleavage peptides).

As the matrix, for example, α-cyano-4-hydroxycinnamic acid (CHCA), 2,5-dihydroxybenzoic acid (2,5-DHB), sinapic acid, 3-aminoquinoline (3-AQ) or the like can be used.

The matrix solvent can be selected from the group consisting of, for example, acetonitrile (ACN), trifluoroacetic acid (TFA), methanol, ethanol and water, and used. More specifically, an ACN-TFA aqueous solution, an ACN aqueous solution, methanol-TFA aqueous solution, a methanol aqueous solution, an ethanol-TFA aqueous solution, an ethanol solution or the like can be used. The concentration of ACN in the ACN-TFA aqueous solution can be, for example, 10 to 90% by volume, the concentration of TFA can be, for example, 0.05 to 1% by volume, preferably 0.05 to 0.1% by volume.

The matrix concentration can be, for example, 0.1 to 50 mg/mL, preferably 0.1 to 20 mg/mL, or 0.3 to 20 mg/mL, further preferably 0.5 to 10 mg/mL.

In the case of employing MALDI mass spectrometry as a detecting system, a matrix additive (comatrix) is preferably used together. The matrix additive can be appropriately selected by a person skilled in the art depending on the analysis subject (APP cleavage peptides) and/or the matrix. For example, as the matrix additive, a phosphonic acid group-containing compound can be used. Specific examples of a compound containing one phosphonic acid group include phosphonic acid, methylphosphonic acid, phenylphosphonic acid, 1-naphthylmethylphosphonic acid, and the like. Specific examples of a compound containing two or more phosphonic acid groups include methylenediphosphonic acid (MDPNA), ethylenediphosphonic acid, ethane-1-hydroxy-1,1-diphosphonic acid, nitrilotriphosphonic acid, ethylenediaminetetraphosphonic acid, and the like. Among the aforementioned phosphonic acid group-containing compounds, compounds having two or more, preferably two to four phosphonic acid groups in one molecule are preferred.

The use of the phosphonic acid group-containing compound is useful, for example, when metal ions of the washing solution remaining on the surface of the antibody-immobilizing carrier are contaminated into the eluate after the dissociating step. The metal ions adversely affect on the background in the mass spectrometry. The use of the phosphonic acid group-containing compound is effective for suppressing such an adverse affect. As described above, as well as washing with the use of an aqueous solution containing ammonium ions in the washing step, the use of the phosphonic acid group-containing compound is preferable for improvement of S/N ratio.

Besides the aforementioned matrix additive, a more common additive, for example, a substance that is selected from the group consisting of ammonium salts and organic bases may be used.

The matrix additive can be prepared as a solution of 0.1 to 10 w/v %, preferably 0.2 to 4 w/v % in water or in a matrix solvent. The matrix additive solution and the matrix solution can be mixed in a volume ratio of, for example, 1:100 to 100:1, preferably 1:10 to 10:1.

EXAMPLES

Hereinafter, the present invention will be described specifically with reference to examples, but is not limited to these examples. In the following, the amount of a matter indicated by % is based on weight when the matter is solid, and based on volume when the matter is liquid unless otherwise indicated.

Example 1 and Comparative Example 1:
Comparison Between Presence and Absence of Organic Solvent in Dissociating Step (1) Production of F(Ab')-Immobilizing Beads APP cleavage peptides in human plasma were bound to an antibody-immobilizing carrier, and the resulting bound body of the APP cleavage peptides and the antibody-immobilizing carrier was washed, and then subjected to the step of dissociating the APP cleavage peptides from the antibody-immobilizing carrier with use of immunoprecipitation. As the antibody-immobilizing carrier used in the immunoprecipitation, F(ab')-immobilizing beads were used. A method for producing F(ab')-immobilizing beads is as follows.

250 μg of anti-amyloid beta antibody (6E10) recognizing the residues 3-8 of amyloid beta as an epitope was digested with 1250 μL of Ficin agarose beads (Thermo) (33% slurry), and 100 μg of anti-amyloid beta antibody (4G8) recognizing the residues 18-22 of amyloid beta as an epitope was digested with 500 ng of lysyl endopeptidase (LysC), and respective digests were separated and collected by a size exclusion chromatography. The fractionated sample was examined by reducing and non-reducing SDS-PAGE, and a fraction corresponding to F(ab')$_2$ was pooled. These F(ab')$_2$ fractions of 6E10 and 4G8 were respectively reduced by 30 mM cysteamine to obtain F(ab'). Then 5 μL (amount of beads 150 μg) of amino magnetic beads (Dynabeads (registered trade name) M-270 Amine: Invitrogen) was prepared, and PEG and the beads were covalently bound by causing NHS groups of SM(PEG)$_{24}$ to react with amino groups bound onto the surface of the beads for 30 minutes at room temperature. To SM(PEG)$_{24}$ bound to magnetic beads, each 0.25 μg of 6E10 F(ab') and 4G8 F(ab') were added at the same time, or 0.5 μg of 6E10 F(ab') alone was added, and they were caused to react for 2 hours at room temperature to covalently bind a maleimide group and a thiol group. Finally, 0.4 mM L-cysteine was caused to react for 30 minutes at room temperature to block maleimide groups. The produced beads to which F(ab') of 6E10 and F(ab') of 4G8 were immobilized (6E10/4G8 F(ab')-immobilizing beads), or beads to which F(ab') of 6E10 alone was immobilized (6E10 F(ab')-immobilizing beads) were stored at 4° C. before use.

(2) Pretreatment of Immunoprecipitation (IP)

Into 50 μL of human plasma (C.C Biotech), an equivalent amount of a binding solution (2% (w/v) n-octyl-β-D-thioglycoside (OTG), 800 mM GlcNAc, 100 mM Tris-HCl, 300 mM NaCl, pH 7.4) was mixed, and then 10% (w/v) PEG 6000 (Nacalai) was added thereto in an amount of 1/50 of that of the human plasma (for example, 0.5 μL of 10% (w/v) PEG 6000 with respect to 50 μL of human plasma). A precipitate contained in this plasma sample was removed by filter centrifugation using Ultrafree-MC, DV 0.65 μm, centrifugal filter devices (Millipore, Cork, IR). Protein G Plus Agarose (50% slurry; Pierce, Rockford, Ill.) was washed once with H$_2$O, and then washed three times with a washing solution (1% (w/v) OTG, 50 mM Tris-HCl, 150 mM NaCl, pH 7.4). The amount of the Protein G Plus Agarose (50% slurry) used herein is twice as much as that of the human plasma (for example, 100 μL of Protein G Plus Agarose with respect to 50 μL of human plasma). The volume of H$_2$O and that of the washing solution used for washing the Protein G Plus Agarose are each 4/5 of that of Protein G Plus Agarose per single washing (for example, 80 µL of H₂O and 80 µL of washing solution with respect to 100 µL of Protein G Plus Agarose). By mixing the foregoing plasma sample after removal of precipitate with the Protein G Plus Agarose and mingling the mixture by inversion at 4° C. for 1 hour, antibodies contained in the plasma were caused to bind with the Protein G Plus Agarose. Then, the Protein G Plus Agarose was removed from the plasma sample.

(3) Immunoprecipitation (IP) (Binding, Dissociation and Elution of APP Cleavage Peptides by F(Ab')-Immobilizing Beads from Human Plasma)

Into 150 µg of 6E10/4G8 F(ab')-immobilizing beads that were washed twice with an OTG-glycine buffer (1% (w/v) OTG, 50 mM glycine, pH 2.8) and three times with 100 µL of the washing solution, the plasma sample from which antibodies were removed by the foregoing pretreatment was mixed and the mixture was mingled by inversion at 4° C. for 1 hour to cause APP cleavage peptides to bind with the beads. Then, a washing operation by stirring the beads with 500 µL of the washing solution was conducted once, and a washing operation by stirring the beads with 100 µL of the washing solution was conducting four times. Further, after conducting a washing operation by stirring the beads with 20 µL of H₂O once, the beads were stirred in each eluent in the following two conditions: the condition of using 5 µL of 3 mM hydrochloric acid as an eluent [Comparative Example 1, FIG. 2(A)] or the condition of using 5 µL of 50% (v/v) acetonitrile containing 3 mM as an eluent [Example 1, FIG. 2(B)], and thus the APP cleavage peptides bound to the 6E10/4G8 F(ab')-immobilizing beads were dissociated and released into the eluent. 0.5 µL of the eluate was taken and dropped on a µFocus MALDI Plate™ 900 µm (Hudson Surface Technology, Inc., Fort Lee, N.J.).

(4) MALDI-TOF MS (Detection of Eluted APP Cleavage Peptides by MALDI-TOF MS)

MALDI-TOF MS was employed in the detecting step. The mass spectrum data was acquired by Linear TOF in a positive ion mode by using AXIMA (registered trade name) Performance (Shimadzu/KRATOS, Manchester, UK). Each of 2500 shots was integrated per one well. As a matrix for Linear TOF, α-cyano-4-hydroxycinnamic acid (CHCA) was used. A matrix solution was prepared by dissolving 5 mg of CHCA in 1 mL of 70% (v/v) acetonitrile. As a matrix additive, 2% (w/v) methanediphosphonic acid (MDPNA) was used. On a µFocus MALDI plate, 0.5 µL of a 5 mg/mL CHCA solution and 0.5 µL of 2% (w/v) MDPNA were added to the eluate.

The method employed in the present example is called IP-MS because detection by mass spectrometry is conducted after immunoprecipitation.

The standard of the detection limit of the peak was an S/N ratio of not less than 3. A m/z value of Linear TOF was indicated by an average mass of peaks. The m/z value was calibrated by using human angiotensin II, human ACTH fragment 18-39, bovine insulin oxidized beta-chain, and bovine insulin as external standards.

The antibody-antigen binding is stabilized by the combination of hydrogen bond, Coulomb's electrostatic force, van der Waals force, and hydrophobic bond. As a condition for dissociating the antigen from the antibody, an acidic solution is generally used. However, only use of an acidic solution is insufficient for dissociating the antigen from the antibody. For cleaving the hydrophobic bond, the elution effect of Aβ1-40 by addition of 50% (v/v) acetonitrile as an organic solvent was examined.

Figure 2:
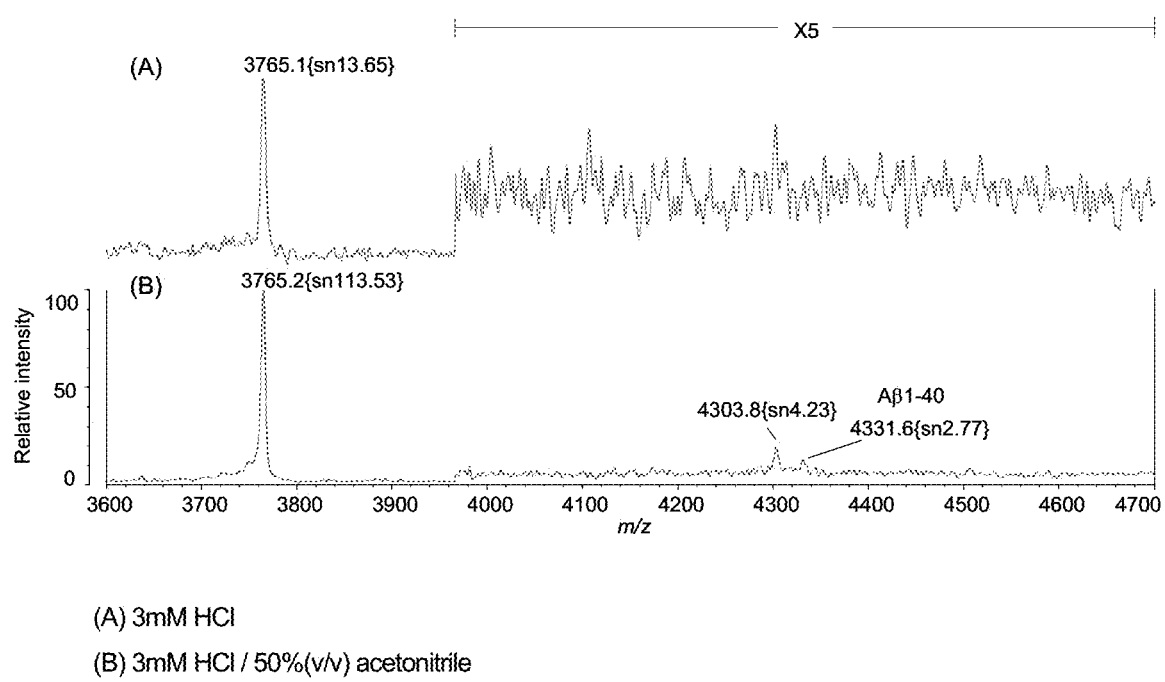
FIG. 2(B) shows a mass spectrum in Example 1.
FIG. 2(A) shows a mass spectrum in Comparative Example 1. The horizontal axis indicates m/z, and the vertical axis indicates relative intensity of ion.

FIG. 2(B) shows a mass spectrum in Example 1, and FIG. 2(A) shows a mass spectrum in Comparative Example 1. As shown in FIG. 2(B), when elution was conducted with 50% (v/v) acetonitrile containing 3 mM hydrochloric acid, the S/N ratio was 2.77, but a peak of Aβ1-40 was observed in the mass spectrum. On the other hand, as shown in FIG. 2(A), when elution was conducted with 3 mM hydrochloric acid (not containing acetonitrile), a peak of Aβ1-40 was not observed in the mass spectrum. This revealed that higher elution efficiency is obtained not only by using acid but also an organic solvent for dissociating APP cleavage peptides from beads to which the APP cleavage peptides are bound.

However, a molecule (m/z: 3765) that was non-specifically bound to 6E10/4G8 F(ab')-immobilizing beads was also eluted more abundantly and detected as a strong signal together with Aβ1-40. The grounds for regarding the peak appearing at m/z: 3765 as a non-specific peak will be described later.

Example 2

Comparison Between Presence and Absence of Ammonium Acetate Buffer in Washing Step of Bound Body of APP Cleavage Peptides and Antibody-Immobilizing Carrier As the washing solution used in the washing step, buffers such as a Tris buffer and a phosphate buffer are often used, and a cationic metal element such as potassium or sodium is contained in the solution. Since contamination of a cationic ion metal element in MALDI-TOF MS measurement reduces a signal of a target peak, it is necessary to avoid contamination of a metal element as much as possible. As a method of avoiding contamination of a cationic ion metal element in MALDI-TOF MS measurement, washing with an ammonium acetate buffer was added in the washing step. Since ammonium ions are volatile, they little reduce a signal of MALDI-TOF MS. After washing with a washing solution (1% (w/v) OTG, 50 mM Tris-HCl, 150 mM NaCl, pH 7.4), an ammonium acetate buffer was used for the purpose of removing a cationic ion metal element in the remaining washing solution. Further, since presence of a surfactant in a solution facilitates accumulation of 6E10/4G8 F(ab')-immobilizing beads to the magnet, and facilitates the washing operation, 0.1% (w/v) OTG was also added to the ammonium acetate buffer.

A pretreatment of immunoprecipitation, and immunoprecipitation were conducted in the following manner.

Into 500 µL of human plasma (C.C Biotech), an equivalent amount of a binding solution (2% (w/v) n-octyl-β-D-thioglycoside (OTG), 800 mM GlcNAc, 100 mM Tris-HCl, 300 mM NaCl, pH 7.4) was mixed, and then 10 µL of 10% (w/v) PEG 6000 was added thereto. A precipitate contained in this plasma sample was removed by filter centrifugation using Ultrafree-MC, DV 0.65 µm, centrifugal filter devices. 1000 µL of Protein G Plus Agarose was washed once with H₂O, and then washed three times with a washing solution (1% (w/v) OTG, 50 mM Tris-HCl, 150 mM NaCl, pH 7.4). By mixing the foregoing plasma sample with this Protein G Plus Agarose and mingling the mixture by inversion at 4° C. for 1 hour, antibodies contained in the plasma were caused to bind with the Protein G Plus Agarose. Then, the Protein G Plus Agarose was removed from the plasma sample.

Into 150 µg of 6E10/4G8 F(ab')-immobilizing beads that were washed twice with an OTG-glycine buffer (1% (w/v) OTG, 50 mM glycine, pH 2.8) and three times with 100 µL of the washing solution, the plasma sample from which antibodies were removed was mixed and the mixture was mingled by inversion at 4° C. for 1 hour to cause APP cleavage peptides to bind with the beads. Then, a washing operation by stirring the beads with 1000 μL of the washing solution was conducted once, and a washing operation by stirring the beads with 100 μL of the washing solution was conducted four times. Then, a washing operation by stirring the beads with 20 μL of a 0.1% (w/v) OTG/200 mM ammonium acetate buffer (pH 7.4) was conducted twice. At this time, the treatment was conducted in the following two ways: the case where the step of washing with the ammonium acetate buffer twice was added (FIG. 3(B)) and the case where the above step was not added (FIG. 3(A)). Further, after conducting a washing operation by stirring the beads with 20 μL of H₂O once, the beads were stirred in 5 μL of 50% (v/v) acetonitrile containing 3 mM hydrochloric acid, and thus the APP cleavage peptides bound to the 6E10/4G8 F(ab')-immobilizing beads were dissociated and eluted. 0.5 μL of the eluate was taken and dropped on a μFocus MALDI Plate™ 900 μm.

Figure 3:
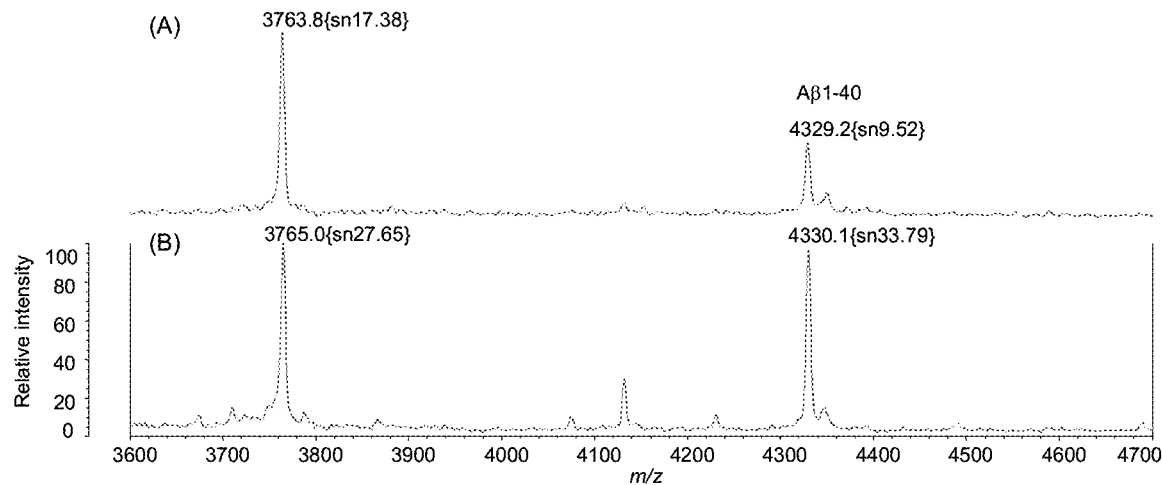
FIG. 3 shows mass spectra in Example 2.

FIG. 3 shows mass spectra in Example 2, FIG. 3(B) shows a mass spectrum when washing with an ammonium acetate buffer (pH 7.4) was added, FIG. 3(A) shows a mass spectrum when washing with an ammonium acetate buffer (pH 7.4) was not added. As shown in FIGS. 3(A) and (B), washing with 0.1% (w/v) OTG/200 mM ammonium acetate buffer (pH 7.4) resulted in increase in S/N ratio in both of the peak of Aβ1-40 and the non-specific peak (m/z: 3765). This revealed that washing with 0.1% (w/v) OTG/200 mM ammonium acetate buffer (pH 7.4) is effective.

Example 3

Improvement in S/N Ratio Depending on Concentration of Matrix Used in MALDI-TOF MS By optimizing the concentration of a matrix and/or the concentration of a matrix additive for use depending on the peptide amount to be measured, an excellent MS signal can be obtained. The concentrations of CHCA and MDPNA were examined.

A pretreatment of immunoprecipitation, and immunoprecipitation were conducted in the following manner.

Into 250 μL of human plasma (C.C Biotech), an equivalent amount of a binding solution (2% (w/v) n-octyl-β-D-thioglycoside (OTG), 800 mM GlcNAc, 100 mM Tris-HCl, 300 mM NaCl, pH 7.4) was mixed, and then 5 μL of 10% (w/v) PEG 6000 was added thereto. A precipitate contained in this plasma sample was removed by filter centrifugation using Ultrafree-MC, DV 0.65 μm, centrifugal filter devices. 500 μL of Protein G Plus Agarose was washed once with H₂O, and then washed three times with a washing solution (1% (w/v) OTG, 50 mM Tris-HCl, 150 mM NaCl, pH 7.4). By mixing the foregoing plasma sample with this Protein G Plus Agarose and mingling the mixture by inversion at 4° C. for 1 hour, antibodies contained in the plasma were caused to bind with the Protein G Plus Agarose. Then, the Protein G Plus Agarose was removed from the plasma sample.

Into 150 μg of 6E10/4G8 F(ab')-immobilizing beads that were washed twice with an OTG-glycine buffer (1% (w/v) OTG, 50 mM glycine, pH 2.8) and three times with 100 μL of the washing solution, the plasma sample from which antibodies were removed was mixed and the mixture was mingled by inversion at 4° C. for 1 hour to cause APP cleavage peptides to bind with the beads. Then, a washing operation by stirring the beads with 500 μL of the washing solution was conducted once, and a washing operation by stirring the beads with 100 μL of the washing solution was conducted four times. Then, a washing operation by stirring the beads with 20 μL of a 0.1% (w/v) OTG/200 mM ammonium acetate buffer (pH 7.4) was conducted twice. Further, after conducting a washing operation by stirring the beads with 20 μL of H₂O once, the beads were stirred in 5 μL of 50% (v/v) acetonitrile containing 3 mM hydrochloric acid, and thus the APP cleavage peptides bound to the 6E10/4G8 F(ab')-immobilizing beads were dissociated and eluted. 0.5 μL of the eluate was taken and dropped on a μFocus MALDI Plate™ 900 μm.

A matrix solution and a matrix additive solution having the following concentrations were used and mixed with an elution sample.

Figure 4:
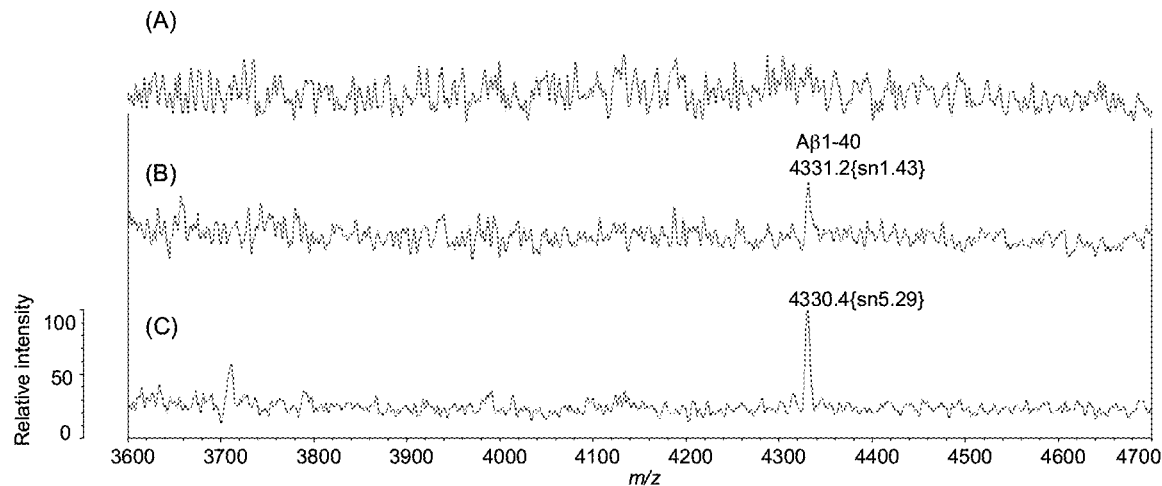
FIG. 4 shows mass spectra in Example 3, and FIGS. 4(A) to (C) each show mass spectra when a matrix solution and a matrix additive solution having the following concentrations are used. (A) 0.5 μL of 5 mg/mL CHCA solution, and 0.5 μL of 2% (w/v) MDPNA (B) 0.5 μL of 1.5 mg/mL CHCA solution, and 0.5 μL of 0.6% (w/v) MDPNA (C) 0.5 μL of 0.5 mg/mL CHCA solution, and 0.5 μL of 0.2% (w/v) MDPNA

(A) 0.5 μL of 5 mg/mL CHCA solution and 0.5 μL of 2% (w/v) MDPNA
(B) 0.5 μL of 1.5 mg/mL CHCA solution and 0.5 μL of 0.6% (w/v) MDPNA
(C) 0.5 μL of 0.5 mg/mL CHCA solution and 0.5 μL of 0.2% (w/v) MDPNA FIG. 4 shows mass spectra in Example 3, FIG. 4(A) shows a mass spectrum in the case of the aforementioned (A), FIG. 4(B) shows a mass spectrum in the case of the aforementioned (B), and FIG. 4(C) shows a mass spectrum in the case of the aforementioned (C). As shown in FIGS. 4(A) to (C), the best S/N ratio of Aβ1-40 was observed in the combination of (C) 0.5 μL of 0.5 mg/mL CHCA solution and 0.5 μL of 0.2% (w/v) MDPNA.

Example 4 and Comparative Example 2:
Comparison of Organic Solvent Concentration in Dissociating Step Acetonitrile concentration that is optimum for elution was examined.

A pretreatment of immunoprecipitation, and immunoprecipitation were conducted in the following manner.

Into 250 μL of human plasma (Tennessee Blood Services), an equivalent amount of a binding solution (0.2% (w/v) DDM, 0.2% (w/v) NTM, 800 mM GlcNAc, 100 mM Tris-HCl, 300 mM NaCl, pH 7.4) was mixed. A precipitate contained in this plasma sample was removed by filter centrifugation using Ultrafree-MC, DV 0.65 μm, centrifugal filter devices. 500 μL of Protein G Plus Agarose was washed once with H₂O, and then washed three times with a washing solution (0.1% (w/v) DDM, 0.1% (w/v) NTM, 50 mM Tris-HCl, 150 mM NaCl, pH 7.4). By mixing the foregoing plasma sample with this Protein G Plus Agarose and mingling the mixture by inversion at 4° C. for 1 hour, antibodies contained in the plasma were caused to bind with the Protein G Plus Agarose. Then, the Protein G Plus Agarose was removed from the plasma sample.

Figure 5:
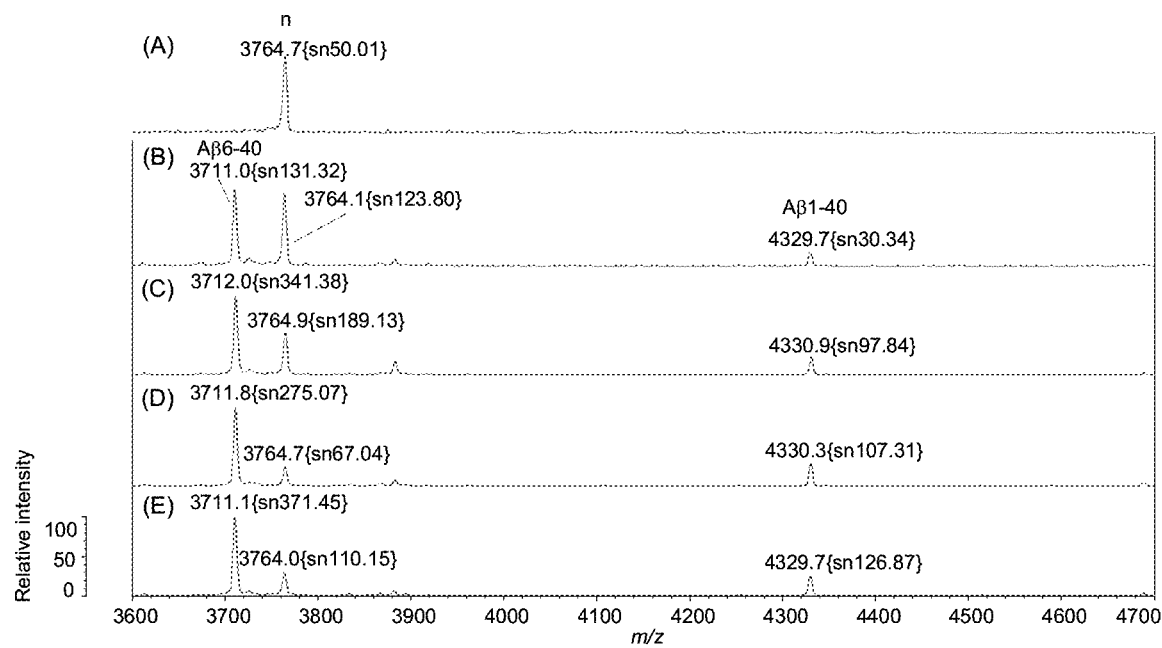
FIG. 5 shows mass spectra in Example 4 and Comparative Example 2, and FIGS. 5(A) to (E) each show mass spectra when the following eluents are used. (A) 5 mM HCl (Comparative Example) (B) 5 mM HCl/20% (v/v) acetonitrile (C) 5 mM HCl/25% (v/v) acetonitrile (D) 5 mM HCl/50% (v/v) acetonitrile (E) 5 mM HCl/70% (v/v) acetonitrile

Into 150 μg of 6E10/4G8 F(ab')-immobilizing beads that were washed twice with an OTG-glycine buffer (1% (w/v) OTG, 50 mM glycine, pH 2.8) and three times with 100 μL of the washing solution, the plasma sample from which antibodies were removed was mixed and the mixture was mingled by inversion at 4° C. for 1 hour to cause APP cleavage peptides to bind with the beads. Then, a washing operation by stirring the beads with 500 μL of the washing solution was conducted once, and a washing operation by stirring the beads with 100 μL of the washing solution was conducted four times. Then, a washing operation by stirring the beads with 20 μL of a 50 mM ammonium acetate buffer (pH 7.4) was conducted twice. Further, after conducting a washing operation by stirring the beads with 20 μL of H₂O once, the APP cleavage peptides bound to the 6E10/4G8 F(ab')-immobilizing beads were dissociated and eluted with 2.5 μL of five kinds of eluents. 0.5 μL of the eluate was taken and dropped on a µFocus MALDI Plate™ 900 µm, and 0.5 µL of a 0.5 mg/mL CHCA solution and 0.5 µL of 0.2% (w/v) MDPNA were mixed. Regarding the mass spectrum data, each of 16000 shots was integrated per one well. As the eluent, the following five kinds were used.
(A) 5 mM HCl (Comparative Example)
(B) 5 mM HCl/20% (v/v) acetonitrile
(C) 5 mM HCl/25% (v/v) acetonitrile
(D) 5 mM HCl/50% (v/v) acetonitrile
(E) 5 mM HCl/70% (v/v) acetonitrile FIG. 5 shows mass spectra in Example 4 and Comparative Example 2, FIG. 5(A) shows a mass spectrum in the case of the aforementioned (A), FIG. 5(B) shows a mass spectrum in the case of the aforementioned (B), FIG. 5(C) shows a mass spectrum in the case of the aforementioned (C), FIG. 5(D) shows a mass spectrum in the case of the aforementioned (D), and FIG. 5(E) shows a mass spectrum in the case of the aforementioned (E). As shown in FIGS. 5(A) to (E), a signal of Aβ1-40 could not be detected at all only with 5 mM HCl. By adding acetonitrile to 5 mM HCl, it became possible to detect a signal of Aβ1-40, and an excellent signal of Aβ1-40 was obtained in 25, 50, 70% (v/v) acetonitrile.

Example 5: Non-Specific Peak Derived from Plasma Detected by MS

Verification was conducted whether or not peaks around m/z: 3765 detected in mass spectra obtained in Examples above were caused by non-specific adsorption of molecules derived from a plasma sample with carrier beads.

First, a sample obtained with dissociation and elution by subjecting 150 µg of 6E10/4G8 F(ab')-immobilizing beads to a dissociating step using 2.5 µL, of 70% (v/v) acetonitrile containing 5 mM hydrochloric acid was measured by MS, but a peak of m/z: 3765 was not detected (FIG. 6(A)). This revealed that a peak of m/z: 3765 is not derived from a molecule dissociated from 6E10/4G8 F(ab')-immobilizing beads themselves and eluted.

Next, Cysteine-PEG$_{24}$ beads produced without binding 6E10 and 4G8 in production of F(ab')-immobilizing beads in Example 1 were prepared. Using 150 µg of Cysteine-PEG$_{24}$ beads, immunoprecipitation was conducted.

A pretreatment of immunoprecipitation, and immunoprecipitation were conducted in the following manner.

Into 250 µL of human plasma (C.C Biotech), an equivalent amount of a binding solution (1% (w/v) n-octyl-β-D-thioglycoside (OTG), 800 mM GlcNAc, 100 mM Tris-HCl, 300 mM NaCl, pH 7.4) was mixed, and then 5 µL of 10% (w/v) PEG 6000 was added thereto. A precipitate contained in this plasma sample was removed by filter centrifugation using Ultrafree-MC, DV 0.65 µm, centrifugal filter devices. 500 µL of Protein G Plus Agarose was washed once with H$_2$O, and then washed three times with a washing solution (0.5% (w/v) OTG, 50 mM Tris-HCl, 150 mM NaCl, pH 7.4). By mixing the foregoing plasma sample with this Protein G Plus Agarose and mingling the mixture by inversion at 4° C. for 1 hour, antibodies contained in the plasma were caused to bind with the Protein G Plus Agarose. Then, the Protein G Plus Agarose was removed from the plasma sample.

Into 150 µg of Cysteine-PEG$_{24}$ beads or 6E10/4G8 F(ab')-immobilizing beads that were washed twice with an OTG-glycine buffer (1% (w/v) OTG, 50 mM glycine, pH 2.8) and three times with 100 µL of the washing solution, the plasma sample from which antibodies were removed was mixed and the mixture was mingled by inversion at 4° C. for 1 hour. Then, a washing operation by stirring the beads with 500 µL of the washing solution was conducted once, and a washing operation by stirring the beads with 100 µL of the washing solution was conducted four times. Then, a washing operation by stirring the beads with 20 µL of a 0.10 (w/v) OTG/200 mM ammonium acetate buffer (pH 7.4) was conducted twice. Further, after conducting a washing operation by stirring the beads with 20 µL of H$_2$O once, the beads were stirred in 2.5 µL of 70% (v/v) acetonitrile containing 5 mM hydrochloric acid, and thus molecules bound to Cysteine-PEG$_{24}$ beads or 6E10/4G8 F(ab')-immobilizing beads were dissociated and eluted. 0.5 µL of the eluate was dropped on a µFocus MALDI Plate™ 900 µm, and 0.5 µL of a 0.5 mg/mL CHCA solution and 0.5 µL of 0.2% (w/v) MDPNA were mixed. Regarding the mass spectrum data, each of 16000 shots was integrated per one well.

Figure 6:
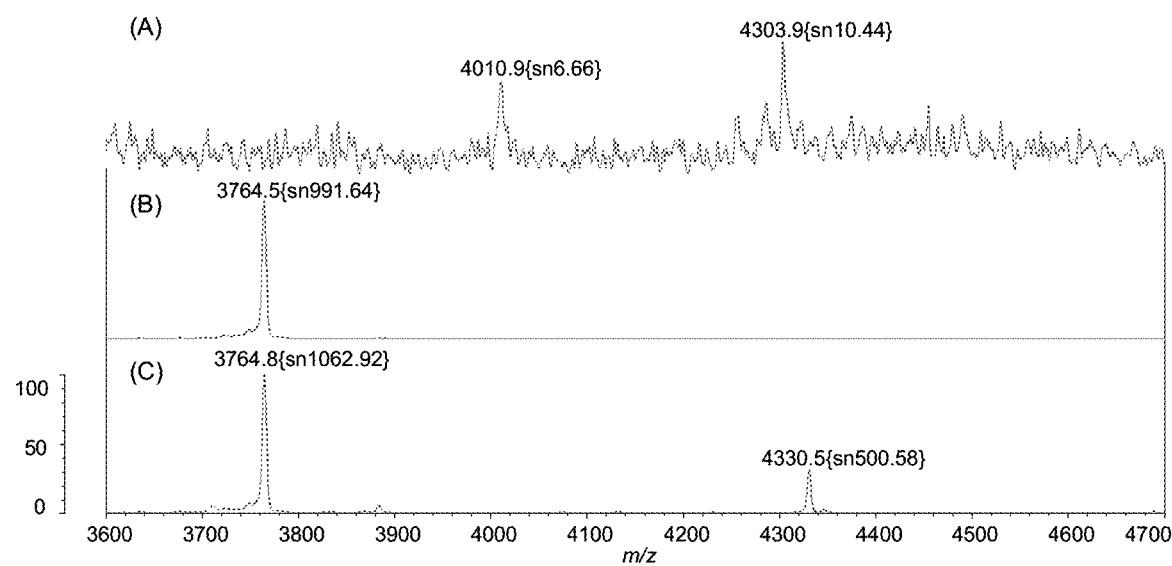
FIG. 6 shows mass spectra in Example 5.

FIG. 6 shows mass spectra in Example 5, and FIG. 6(A) shows a mass spectrum obtained by conducting an eluting step using 2.5 µL of 70% (v/v) acetonitrile containing 5 mM hydrochloric acid for 150 µg of 6E10/4G8 F(ab')-immobilizing beads, FIG. 6(B) shows a mass spectrum obtained by conducting IP-MS using 150 µg of Cysteine-PEG$_{24}$ beads for 250 µL of a human plasma sample, and FIG. 6(C) shows a mass spectrum obtained by conducting IP-MS using 150 µg of 6E10/4G8 F(ab')-immobilizing beads for 250 µL of a human plasma sample.

As shown in FIG. 6(B), a strong peak of m/z: 3765 was detected. The peak of m/z: 3765 was also detected in immunoprecipitation using 150 µg of 6E10/4G8 F(ab')-immobilizing beads (FIG. 6(C)). The results shown in FIGS. 6(A) to (C) demonstrated that the peak of m/z: 3765 is derived from a molecule of a human plasma sample, and the molecule is detected by MS with non-specific adsorption to carrier beads, and dissociation and elution in the dissociating step.

Example 6: Influence on MS Signal Depending on Kinds of Surfactants Contained in Binding Solution and Washing Solution Example 5 revealed that a peak around m/z: 3765 detected in a mass spectrum is derived from a molecule of a human plasma sample that is non-specifically adsorbed to carrier beads. While the surfactant added to the binding solution and the washing solution is used for suppressing non-specific binding, the binding force between antigen and antibody and the non-specific adsorption vary depending on the kind of the surfactant. Influence on the MS spectrum by using the following surfactants besides OTG was examined. In [ ], a critical micelle concentration (cmc) of each surfactant is shown.
(1) n-Octyl-β-D-thioglucoside (OTG) [cmc: 0.278%]
(2) n-Octyl-β-D-glucoside (OG) [cmc: 0.731%]
(3) n-Decyl-β-D-maltoside (DM) [cmc: 0.087%]
(4) n-Dodecyl-β-D-maltoside (DDM) [cmc: 0.009%]
(5) n-Nonyl-β-D-thiomaltoside (NTM) [cmc: 0.116%]

Binding solutions and washing solution containing the aforementioned surfactants were produced in the following manner, and immunoprecipitation was conducted on 250 µL of a human plasma sample (Tennessee Blood Services) by using these binding solutions and washing solutions.

A pretreatment of immunoprecipitation, and immunoprecipitation were conducted in the following manner.

Into 250 µL of human plasma (Tennessee Blood Services), an equivalent amount of a binding solution was mixed. A precipitate contained in this plasma sample was removed by filter centrifugation using Ultrafree-MC, DV 0.65 µm, centrifugal filter devices. 500 µL of Protein G Plus Agarose was washed once with H$_2$O, and then washed three times with a washing solution. By mixing the foregoing plasma sample with this Protein G Plus Agarose and mingling the mixture by inversion at 4° C. for 1 hour, antibodies contained in the plasma were caused to bind with the Protein G Plus Agarose. Then, the Protein G Plus Agarose was removed from the plasma sample.

Into 150 μg of 6E10/4G8 F(ab')-immobilizing beads that were washed twice with an OTG-glycine buffer (1% (w/v) OTG, 50 mM glycine, pH 2.8) and three times with 100 μL of the washing solution, the plasma sample from which antibodies were removed was mixed and the mixture was mingled by inversion at 4° C. for 1 hour to cause APP cleavage peptides to bind with the beads. Then, a washing operation by stirring the beads with 500 μL of the washing solution was conducted once, and a washing operation by stirring the beads with 100 μL of the washing solution was conducted four times. Then, a washing operation by stirring the beads with 20 μL of a 50 mM ammonium acetate buffer (pH 7.4) was conducted twice. Further, after conducting a washing operation by stirring the beads with 20 μL of $H_2O$ once, the APP cleavage peptides bound to the 6E10/4G8 F(ab')-immobilizing beads were dissociated and eluted with 2.5 μL of 70% (v/v) acetonitrile containing 5 mM hydrochloric acid. 0.5 μL of the eluate was taken and dropped on a μFocus MALDI Plate™ 900 μm, and 0.5 μL of a 0.5 mg/mL CHCA solution and 0.5 μL of 0.2% (w/v) MDPNA were mixed. Regarding the mass spectrum data, each of 16000 shots was integrated per one well. The binding solution and the washing solution used at this time are as shown in the following (A) to (E).

(A) Binding solution (1% (w/v) OTG, 800 mM GlcNAc, 100 mM Tris-HCl, 300 mM NaCl, pH 7.4),
   Washing solution (0.5% (w/v) OTG, 50 mM Tris-HCl, 150 mM NaCl, pH 7.4)
(B) Binding solution (3% (w/v) OG, 800 mM GlcNAc, 100 mM Tris-HCl, 300 mM NaCl, pH 7.4),
   Washing solution (1.5% (w/v) OG, 50 mM Tris-HCl, 150 mM NaCl, pH 7.4)
(C) Binding solution (0.3% (w/v) DM, 800 mM GlcNAc, 100 mM Tris-HCl, 300 mM NaCl, pH 7.4),
   Washing solution (0.15% (w/v) DM, 50 mM Tris-HCl, 150 mM NaCl, pH 7.4)
(D) Binding solution (0.03% (w/v) DDM, 800 mM GlcNAc, 100 mM Tris-HCl, 300 mM NaCl, pH 7.4),
   Washing solution (0.015% (w/v) DDM, 50 mM Tris-HCl, 150 mM NaCl, pH 7.4)
(E) Binding solution (0.4% (w/v) NTM, 800 mM GlcNAc, 100 mM Tris-HCl, 300 mM NaCl, pH 7.4),
   Washing solution (0.2% (w/v) NTM, 50 mM Tris-HCl, 150 mM NaCl, pH 7.4)

FIG. 7 shows mass spectra in Example 6, FIG. 7(A) shows a mass spectrum in the case of the aforementioned (A), FIG. 7(B) shows a mass spectrum in the case of the aforementioned (B), FIG. 7(C) shows a mass spectrum in the case of the aforementioned (C), FIG. 7(D) shows a mass spectrum in the case of the aforementioned (D), and FIG. 7(E) shows a mass spectrum in the case of the aforementioned (E).

As shown in FIGS. 7(A) to (E), in the solution containing OG, a peak derived from a non-specifically adsorbed molecule (hereinafter, also referred to as a non-specific peak) (m/z: 3764.5) was detected very strongly, and an Aβ1-40 signal was slightly stronger compared with the case of OTG (FIG. 7(B)). In the solution containing DM, a non-specific peak (m/z: 3765.1) was strongly detected, and an Aβ1-40 signal was also slightly strong (FIG. 7(C)). In the solution containing DDM, a non-specific peak (m/z: 3764.8) was strongly detected, and an Aβ1-40 signal was also strongly detected (FIG. 7(D)). In the solution containing NTM, a non-specific peak (m/z: 3764.8) was not detected, and an Aβ1-40 signal was reduced in comparison with the case of OTG (FIG. 7(E)). These results revealed that both of a non-specific peak and a signal of Aβ1-40 are strongly detected particularly in DDM, and on the contrary, NTM has the effect of suppressing both of a non-specific peak and a signal of Aβ1-40.

Accordingly, it was found that the signal intensity of the peak of Aβ1-40 in the mass spectrum is higher in DDM than in the case of using OTG, and the signal intensity of the non-specific peak is also high. For this reason, immunoprecipitation was conducted with a higher DDM concentration for the purpose of suppressing non-specific adsorption. The compositions of the used binding solution and washing solution are as follows.

(D-1) Binding solution (0.03% (w/v) DDM, 800 mM GlcNAc, 100 mM Tris-HCl, 300 mM NaCl, pH 7.4),
   Washing solution (0.015% (w/v) DDM, 50 mM Tris-HCl, 150 mM NaCl, pH 7.4)
(D-2) Binding solution (0.1% (w/v) DDM, 800 mM GlcNAc, 100 mM Tris-HCl, 300 mM NaCl, pH 7.4),
   Washing solution (0.05% (w/v) DDM, 50 mM Tris-HCl, 150 mM NaCl, pH 7.4)
(D-3) Binding solution (0.3% (w/v) DDM, 800 mM GlcNAc, 100 mM Tris-HCl, 300 mM NaCl, pH 7.4),
   Washing solution (0.15% (w/v) DDM, 50 mM Tris-HCl, 150 mM NaCl, pH 7.4)

Figure 8:
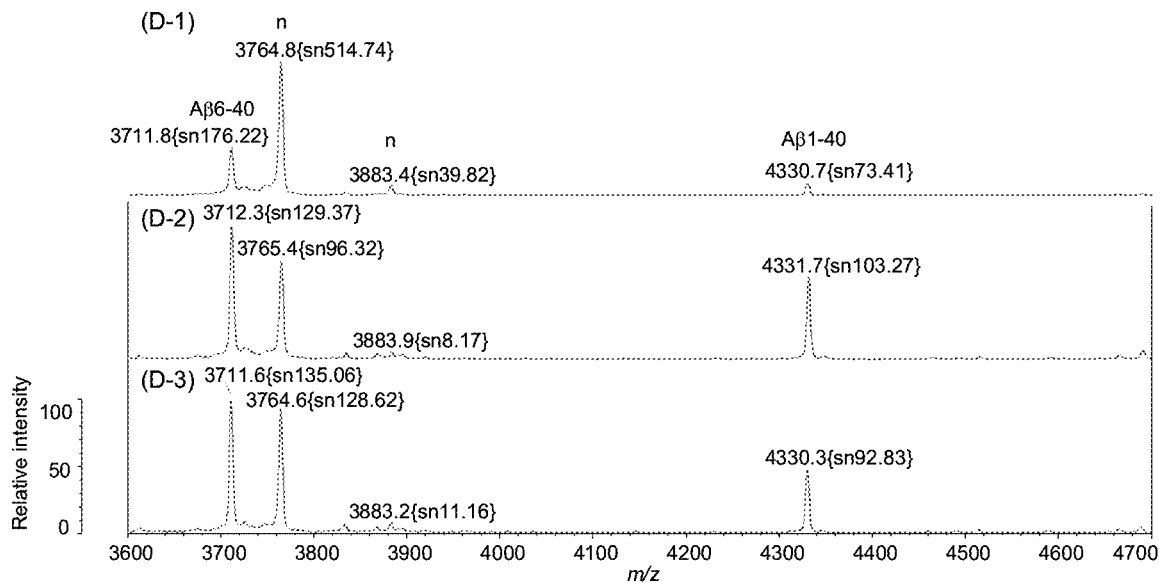
FIG. 8 shows mass spectra in Example 6, and FIG. 8(D-1) to (D-3) each show mass spectra when the following binding solution and washing solution are used. (D-1) binding solution (0.03% (w/v) DDM, 800 mM GlcNAc, 100 mM Tris-HCl, 300 mM NaCl, pH 7.4), washing solution (0.015% (w/v) DDM, 50 mM Tris-HCl, 150 mM NaCl, pH 7.4) (D-2) binding solution (0.1% (w/v) DDM, 800 mM GlcNAc, 100 mM Tris-HCl, 300 mM NaCl, pH 7.4), washing solution (0.05% (w/v) DDM, 50 mM Tris-HCl, 150 mM NaCl, pH 7.4) (D-3) binding solution (0.3% (w/v) DDM, 800 mM GlcNAc, 100 mM Tris-HCl, 300 mM NaCl, pH 7.4), washing solution (0.15% (w/v) DDM, 50 mM Tris-HCl, 150 mM NaCl, pH 7.4)

FIG. 8 shows mass spectra in Example 6, FIG. 8(D-1) shows a mass spectrum in the case of the aforementioned (D-1), FIG. 8(D-2) shows a mass spectrum in the case of the aforementioned (D-2), and FIG. 8(D-3) shows a mass spectrum in the case of the aforementioned (D-3).

By increasing the DDM concentrations in the binding solution and the washing solution from the condition of (D-1) to the condition of (D-2), it was successful in reducing the signal of the non-specific peak (m/z: 3764.8) without suppressing the signal of Aβ1-40 (FIG. 8). The effect was unchanged from the case of (D-2) even when the DDM concentration was further increased to the condition of (D-3).

Next, in FIG. 7, a non-specific peak (m/z: 3764.8) was not detected in NTM, but the signal of Aβ1-40 was simultaneously reduced. For the purpose of heightening the signal of Aβ1-40, immunoprecipitation was conducted by reducing the NTM concentration. The compositions of the used binding solution and washing solution are as follows.

(E-1) Binding solution (0.4% (w/v) NTM, 800 mM GlcNAc, 100 mM Tris-HCl, 300 mM NaCl, pH 7.4),
   Washing solution (0.2% (w/v) NTM, 50 mM Tris-HCl, 150 mM NaCl, pH 7.4)
(E-2) Binding solution (0.3% (w/v) NTM, 800 mM GlcNAc, 100 mM Tris-HCl, 300 mM NaCl, pH 7.4),
   Washing solution (0.15% (w/v) NTM, 50 mM Tris-HCl, 150 mM NaCl, pH 7.4)
(E-3) Binding solution (0.2% (w/v) NTM, 800 mM GlcNAc, 100 mM Tris-HCl, 300 mM NaCl, pH 7.4),
   Washing solution (0.1% (w/v) NTM, 50 mM Tris-HCl, 150 mM NaCl, pH 7.4)

Figure 9:
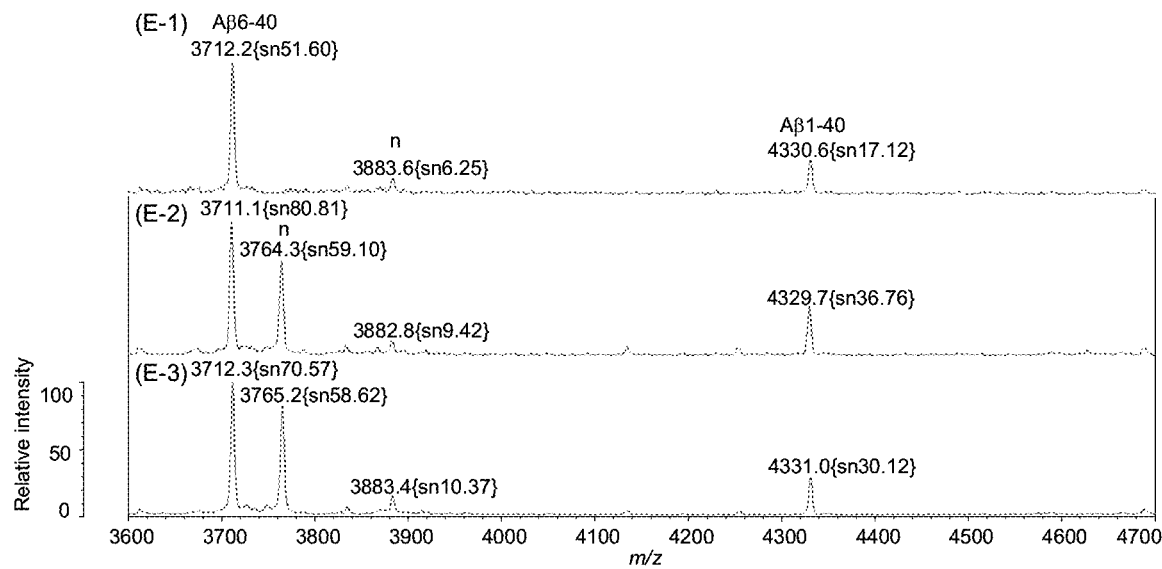
FIG. 9 shows mass spectra in Example 6, and FIG. 9(E-1) to (E-3) each show mass spectra when the following binding solution and washing solution are used. (E-1) binding solution (0.4% (w/v) NTM, 800 mM GlcNAc, 100 mM Tris-HCl, 300 mM NaCl, pH 7.4), washing solution (0.2% (w/v) NTM, 50 mM Tris-HCl, 150 mM NaCl, pH 7.4) (E-2) binding solution (0.3% (w/v) NTM, 800 mM GlcNAc, 100 mM Tris-HCl, 300 mM NaCl, pH 7.4), washing solution (0.15% (w/v) NTM, 50 mM Tris-HCl, 150 mM NaCl, pH 7.4) (E-3) binding solution (0.2% (w/v) NTM, 800 mM GlcNAc, 100 mM Tris-HCl, 300 mM NaCl, pH 7.4), washing solution (0.1% (w/v) NTM, 50 mM Tris-HCl, 150 mM NaCl, pH 7.4)

FIG. 9 shows mass spectra in Example 6, FIG. 9(E-1) shows a mass spectrum in the case of the aforementioned (E-1), FIG. 9(E-2) shows a mass spectrum in the case of the aforementioned (E-2), and FIG. 9(E-3) shows a mass spectrum in the case of the aforementioned (E-3).

By decreasing the NTM concentrations in the binding solution and the washing solution from (E-1) to (E-2), the signal of Aβ1-40 could be increased, and also a non-specific peak (m/z: 3764.8) is detected (FIG. 9). No change from the case of (E-2) was observed even when the NTM concentration was further decreased to the condition of (E-3).

Finally, immunoprecipitation was conducted by using the binding solution and the washing solution each of which DDM having the effect of increasing the signal and NTM having the effect of suppressing a signal are mixed. The compositions of the used binding solution and washing solution are as follows.

(F) Binding solution (0.2% (w/v) DDM, 0.2% (w/v) NTM, 800 mM GlcNAc, 100 mM Tris-HCl, 300 mM NaCl, pH 7.4), Washing solution (0.1% (w/v) DDM, 0.1% (w/v) NTM, 50 mM Tris-HCl, 150 mM NaCl, pH 7.4)

(A) Binding solution (1% (w/v) OTG, 800 mM GlcNAc, 100 mM Tris-HCl, 300 mM NaCl, pH 7.4), Washing solution (0.5% (w/v) OTG, 50 mM Tris-HCl, 150 mM NaCl, pH 7.4)

This (A) is the same as that described above.

Figure 10:
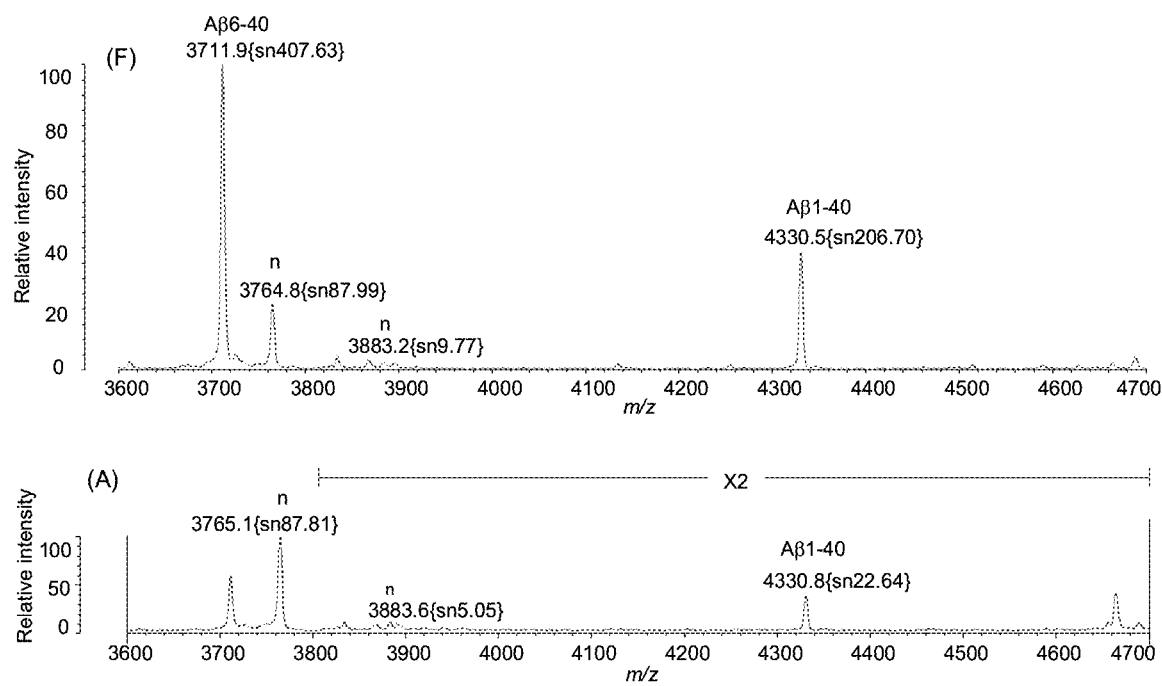
FIG. 10 shows mass spectra in Example 6, and FIGS. 10(A) and (F) each show mass spectra when the following binding solution and washing solution are used. (A) binding solution (1% (w/v) OTG, 800 mM GlcNAc, 100 mM Tris-HCl, 300 mM NaCl, pH 7.4), washing solution (0.5% (w/v) OTG, 50 mM Tris-HCl, 150 mM NaCl, pH 7.4) (F) binding solution (0.2% (w/v) DDM, 0.2% (w/v) NTM, 800 mM GlcNAc, 100 mM Tris-HCl, 300 mM NaCl, pH 7.4)

FIG. 10 shows mass spectra in Example 6, FIG. 10(F) shows a mass spectrum in the case of the aforementioned (F), and FIG. 10(A) shows a mass spectrum in the case of the aforementioned (A). FIG. 10(A) shows the same mass spectrum as in FIG. 7(A) above.

As shown in FIG. 10(F), by using the aforementioned binding solution and washing solution, a spectrum was obtained in which a signal of Aβ1-40 was very strong compared with the case of using OTG shown in FIG. 10(A). Although a non-specific peak could not be completely removed, the non-specific peak (m/z: 3764.8) could be reduced relatively in comparison with the signal of Aβ1-40. Among the surfactants compared and examined herein, it is preferred to use combination of DDM and NTM for detecting signals of APP cleavage peptides.

Example 7 and Comparative Example 3: Example Using 11A50-B10 IgG-Immobilizing Beads The effect of improvement in sensitivity by the immunoprecipitation in the present invention using an antibody-immobilizing carrier other than the F(ab')-immobilizing beads produced in Example 1 was examined. As an antibody-immobilizing carrier other than the F(ab')-immobilizing beads, beads to which an anti-amyloid antibody (11A50-B10) recognizing a C-terminal of amyloid beta (1-40) as an epitope were produced in the following manner.

(1) Production of 11A50-B10 IgG-Immobilizing Beads

An anti-amyloid antibody (11A50-B10) recognizing a C-terminal of amyloid beta (1-40) as an epitope was directly immobilized to beads according to the procedure manual attached to the product of Dynabeads Tosylactivated (Invitrogen). Specifically, in order to bind 7.5 μg of the anti-amyloid beta antibody (11A50-B10) to a tosyl group of 55 μL (amount of beads: 1.66 mg) of Dynabeads Tosylactivated, they were caused to react in a buffer (1.2 M ammonium sulfate, 100 mM phosphate buffer, pH 7.4) at 37° C. for 16 hours. Then, they were caused to react in TBS (150 mM NaCl, 50 mM Tris-HCl, pH 7.4) at 37° C. for 1 hour to be blocked. The produced 11A50-B10 IgG-immobilizing beads were stored at 4° C. before use.

(2) Effect of Improved Method in Immunoprecipitation Using 11A50-B10 IgG-Immobilizing Beads Using the produced antibody-immobilizing carrier, a pretreatment of immunoprecipitation, and immunoprecipitation were conducted in the following manner.

To 250 μL of human plasma (C.C Biotech), an equivalent amount of a binding solution was mixed. A precipitate contained in this plasma sample was removed by filter centrifugation using Ultrafree-MC, DV 0.65 μm, centrifugal filter devices. 500 μL of Protein G Plus Agarose was washed once with H$_2$O, and then washed three times with a washing solution. Then, the foregoing plasma sample was mixed with the Protein G Plus Agarose and the mixture was mingled by inversion 4° C. for 1 hour to cause antibodies contained in the plasma to bind with the Protein G Plus Agarose. Then, the Protein G Plus Agarose was removed from the plasma sample.

Figure 11:
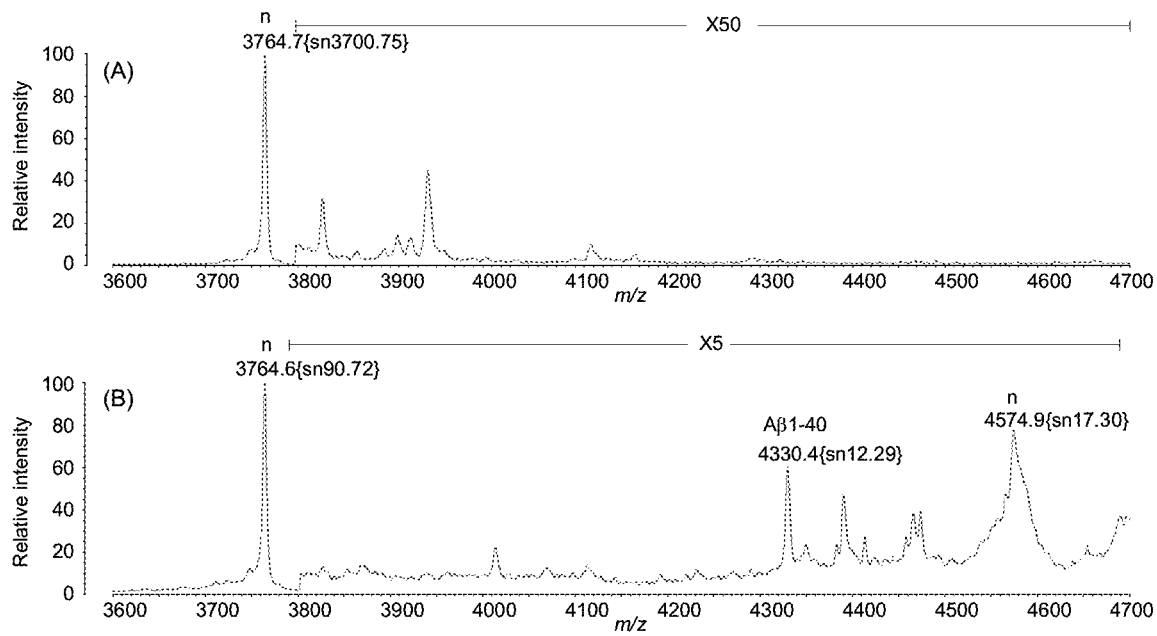
FIG. 11(B) shows a mass spectrum in Example 7.
FIG. 11(A) shows a mass spectrum in Comparative Example 3.

Into 11A50-B10 IgG-immobilizing beads (amount of beads: 300 μg) that were washed twice with an OTG-glycine buffer (1% (w/v) OTG, 50 mM glycine, pH 2.8) and three times with 100 μL of the washing solution, the plasma sample from which antibodies were removed was mixed and the mixture was mingled by inversion at 4° C. for 1 hour to cause APP cleavage peptides to bind with the beads. Then, a washing operation by stirring the beads with 500 μL of the washing solution was conducted once, and a washing operation by stirring the beads with 100 μL of the washing solution was conducted four times. Then, a washing operation by stirring the beads with 20 μL of a 50 mM ammonium acetate buffer (pH 7.4) was conducted twice. Further, after conducting a washing operation by stirring the beads with 20 μL of H$_2$O once, the APP cleavage peptides bound to the 11A50-B10 IgG-immobilizing beads were dissociated and eluted with 2.5 μL of an eluent. 0.5 μL of the eluate was taken and dropped on a μFocus MALDI Plate™ 900 μm. As a matrix, 0.5 μL of a 0.5 mg/mL CHCA solution and 0.5 μL of 0.2% (w/v) MDPNA were added to the eluate on the μFocus MALDI plate. After drying, an MS spectrum was acquired. Regarding the mass spectrum data, each of 16000 shots was integrated per one well (FIG. 11).

Here, the compositions of the binding solution, washing solution, and eluent used in immunoprecipitation are the following (A) (Comparative Example 3: conventional method) and (B) (Example 7: improved method).

(A) Binding solution (2% (w/v) OTG, 800 mM GlcNAc, 100 mM Tris-HCl, 300 mM NaCl, pH 7.4), Washing solution (1% (w/v) OTG, 50 mM Tris-HCl, 150 mM NaCl, pH 7.4), Eluent (5 mM HCl)

(B) Binding solution (0.2% (w/v) DDM, 0.2% (w/v) NTM, 800 mM GlcNAc, 100 mM Tris-HCl, 300 mM NaCl, pH 7.4), Washing solution (0.1% (w/v) DDM, 0.1% (w/v) NTM, 50 mM Tris-HCl, 150 mM NaCl, pH 7.4), Eluent (5 mM HCl/70% (v/v) acetonitrile)

FIG. 11(B) shows a mass spectrum in Example 7, and FIG. 11(A) shows a mass spectrum in Comparative Example 3.

In the conventional method (A) [Comparative Example 3], a signal of Aβ1-40 was not detected at all. In contrast to this, in the improved method (B) [Example 7], a signal of Aβ1-40 could be detected. This indicated that the improvement method has the effect of improving the sensitivity regardless of the kind of the beads and antibody. A non-specific peak was also detected. This is considered as non-specific adsorption of proteins and the like in the plasma because the surface of Dynabeads Tosylactivated is hydrophobic.

Example 8

IP-MS using the present invention was conducted, and the detection and identification of various APP cleavage peptides existing in the human plasma were attempted.

(1) Pretreatment of Immunoprecipitation (IP)

Into 250 μL of human plasma, 250 μL of a binding solution (1% n-octyl-β-D-thioglycoside (OTG), 800 mM GlcNAc, 100 mM Tris-HCl, 300 mM NaCl, pH 7.4) and 5 μL of 10% PEG 6000 were mixed. A precipitate contained in this plasma sample was removed by filter centrifugation using Ultrafree-MC, DV 0.65 μm, centrifugal filter devices. 500 μL of Protein G Plus Agarose (50% slurry; Pierce, Rockford, Ill.) was washed once with 400 μL of H$_2$O, and then washed three times with 400 μL of a washing solution (0.5% OTG, 50 mM Tris-HCl, 150 mM NaCl, pH 7.4). By mixing the foregoing plasma sample with this Protein G Plus Agarose and incubating the mixture at 4° C. for 1 hour, antibodies contained in the plasma were caused to bind with the Protein G Plus Agarose. Then, the Protein G Plus Agarose was removed from the plasma sample.

(2) Immunoprecipitation (IP)

Into 150 μg of 6E10/4G8 F(ab')-immobilizing beads (produced in Example 1) that were washed twice with an OTG-glycine buffer (1% OTG, 50 mM glycine, pH 2.8) and three times with 100 μL of the washing solution, the plasma sample from which antibodies were removed was mixed and the mixture was incubated at 4° C. for 1 hour to cause APP cleavage peptides to bind with the beads. Then, a washing operation by stirring the beads with 500 μL of the washing solution was conducted once, and a washing operation by stirring the beads with 100 μL of the washing solution was conducted four times. Then, a washing operation by stirring the beads with 20 μL of a 50 mM ammonium acetate buffer (pH 7.4) was conducted twice. Further, after conducting a washing operation by stirring the beads with 20 μL of H$_2$O once, the APP cleavage peptides bound to the 6E10/4G8 F(ab')-immobilizing beads were dissociated and eluted with 2.5 μL of 70% acetonitrile containing 5 mM hydrochloric acid. The eluate was dropped on a μFocus MALDI Plate™ 900 μm in the following manner. In the case of measurement by Linear TOF MS, each 0.5 μL of the eluate was dropped into four wells. In the case of measurement by quadrupole ion trap (QIT) reflectron TOF MS employed in identification of the detected peak, 2 μL of the eluate was dropped into one well.

(3) Detection by MALDI-TOF MS

The mass spectrum data was acquired by Linear TOF in a positive ion mode by using AXIMA Performance. In Linear TOF, each of 40 shots was integrated for each point of 400 positions in a raster mode. For identification of the APP cleavage peptides, MS/MS analysis was conducted in a positive ion mode of QIT reflectron TOF by using AXIMA Resonance (Shimadzu/KRATOS). As a matrix for Linear TOF, α-cyano-4-hydroxycinnamic acid (CHCA) was used, and as a matrix for QIT reflectron TOF, 2,5-dihydroxybenzoic acid (DHB) was used. A matrix solution was prepared by dissolving 1 mg of CHCA and 5 mg of DHB respectively in 1 mL of 70% acetonitrile. As a matrix additive, 0.4% methanediphosphonic acid (MDPNA) was used. After mixing an equivalent amount of 0.4% MDPNA into the CHCA solution and the DHB solution, 0.5 μL of the matrix-additive mixture was added to the eluate on a μFocus MALDI plate.

The standard of the detection limit of the peak was an S/N ratio of not less than 3. A m/z value of Linear TOF was indicated by an average mass of peaks, and a m/z value was indicated by monoisotopic ion mass in QIT reflectron TOF. The m/z value was calibrated by using human angiotensin II, human ACTH fragment 18-39, bovine insulin oxidized beta-chain, and bovine insulin as external standards. The peak list of an MS/MS spectrum was prepared by Mascot Distiller (Matrix Science), and analyzed by Mascot software Version 2.4 (Matrix Science). Parameters in Mascot search are as follows: No enzyme, SwissProt database with species limitation (only human), Precursor ion tolerance 0.3 Da, and Fragment ion tolerance 0.4 Da.

Mass spectra obtained in the manner as described above are shown in FIG. 12. FIG. 12(A) shows a mass spectrum of Linear TOF, and FIG. 12(B) shows a mass spectrum of QIT reflectron TOF. In FIGS. 12(A) and (B), "*" indicates a peak of ion corresponding to the mass of a peptide generated by APP cleavage (molecular weight-related ion). Well known APP672-711 (Aβ1-40) and APP672-713 (Aβ1-42) were observed in both of Linear TOF and QIT reflectron TOF. The name of a peptide used herein is expressed, for example, by APP672-711 (Aβ1-40), which means a peptide in which the position 672 is the N-terminal and the position 711 is the C-terminal in the amino acid sequence of APP, and also means a peptide of position 1 to position 40 of peptide which is typically called Aβ. A peptide that is long on the N-terminal side than the first position of Aβ peptide is not expressed as Aβ.

In addition to these peptides (APP672-711 (Aβ1-40) and APP672-713 (Aβ1-42)) which are principal components of a senile plaque of AD, peptides cleaved at the position closer to the N-terminal or C-terminal than APP672-711 (Aβ1-40), and further a novel cleavage APP peptide generated by cleavage at the position closer to the N-terminal than the site where cleavage by secretase occurs were detected. In the mass spectrum measured by QIT reflectron TOF (FIG. 12(B)), four fragment ions indicated by "f" were detected, and these peaks were excluded.

Here, the four fragment ions indicated by "f" are not molecular weight-related ions of the cleavage APP peptides themselves existing in the plasma, but are fragment ions that are cleaved when the molecular weight-related ions of the cleavage APP peptides are measured by QIT reflectron TOF.

(4) MS/MS Analysis of APP Cleavage Peptides Detected in Human Plasma

For identifying the APP cleavage peptides detected by MS, MS/MS analysis was conducted for 20 kinds of peaks among the detected 22 kinds of peaks. For six kinds of peaks, the Mascot score was not less than 20; however, for other peaks, the signals were weak, and thus the Mascot scores were low (Table 2). However, fragment ions generated by cleavage on the C-terminal side of aspartic acid and glutamic acid that are preferentially occurred in CID were detected in every spectrum analyzed by MS/MS (Table 2, FIG. 13 to FIG. 22). Further, when taking into consideration the selectivity by 6E10/4G8 F(ab')-immobilizing beads, the accuracy of a measurement mass value, the antibody 6E10 used, or a sequence containing an epitope of 4G8 in combination, the accuracy of identification of APP cleavage peptides shown in Table 1 to Table 2 is quite high. For the detected two peaks of high mass of the APP cleavage peptides, ion trapping with sufficient selectivity cannot be performed with the device used herein, so that MS/MS data could not be acquired.

When the above data was summarized, it was finally confirmed the existence of 22 kinds of the APP cleavage peptides in the plasma both by the Linear TOF and by the QIT reflectron TOF. Eight kinds of peptides (APP671-711, APP669-709, APP669-710, APP669-711, APP666-709, APP666-711, APP664-711, APP663-711) among these 22 kinds have not been found in human CSF heretofore, and are novel APP cleavage peptides that were found for the first time by the analysis of this study.

APP671-711 (SEQ ID NO: 14):
MDAEFRHDSGYEVHHQKLVFFAEDVGSNKGAIIGLMVGGVV

APP669-709 (SEQ ID NO: 15):
VKMDAEFRHDSGYEVHHQKLVFFAEDVGSNKGAIIGLMVGG

APP669-710 (SEQ ID NO: 17):
VKMDAEFRHDSGYEVHHQKLVFFAEDVGSNKGAIIGLMVGGV

APP669-711 (SEQ ID NO: 18):
VKMDAEFRHDSGYEVHHQKLVFFAEDVGSNKGAIIGLMVGGVV

APP666-709 (SEQ ID NO: 19):
ISEVKMDAEFRHDSGYEVHHQKLVFFAEDVGSNKGAIIGLMVGG

APP666-711 (SEQ ID NO: 20):
ISEVKMDAEFRHDSGYEVHHQKLVFFAEDVGSNKGAIIGLMVGGVV

APP664-711 (SEQ ID NO: 21):
EEISEVKMDAEFRHDSGYEVHHQKLVFFAEDVGSNKGAIIGLMVGGVV
and

APP663-711 (SEQ ID NO: 22):
TEEISEVKMDAEFRHDSGYEVHHQKLVFFAEDVGSNKGAIIGLMVGGVV

Among 22 kinds of the APP cleavage peptides, APP672-711 (Aβ1-40) shows the highest peak, and this is consistent with the results of human CSF indicated in other reports. Also, it is confirmed that APP672-711 (Aβ1-40) detectable by 6E10/4G8 F(ab')-immobilizing beads and APP cleavage peptides such as peptides cleaved at the position closer to the N-terminal than APP672-711 (Aβ1-40) can also be detected by F(ab')-immobilizing beads of 6E10 alone.

TABLE 1

| SEQ ID NO. | Truncated APP variants | Sequence TEEISEVKMDAEFRHDSGYEVHHQKLVFFAEDVGSNKGAIIGLMVGGVVIA<br>663                                              713 |
|---|---|---|
| 1 | APP682-711 (Aβ11-40) | EVHHQKLVFFAEDVGSNKGAIIGLMVGGVV |
| 2 | APP677-709 (Aβ6-38) | HDSGYEVHHQKLVFFAEDVGSNKGAIIGLMVGG |
| 3 | APP676-708 (Aβ5-37) | RHDSGYEVHHQKLVFFAEDVGSNKGAIIGLMVG |
| 4 | APP672-704 (Aβ1-33) | DAEFRHDSGYEVHHQKLVFFAEDVGSNKGAIIG |
| 5 | APP677-711 (Aβ6-40) | HDSGYEVHHQKLVFFAEDVGSNKGAIIGLMVGGVV |
| 6 | APP676-711 (Aβ5-40) | RHDSGYEVHHQKLVFFAEDVGSNKGAIIGLMVGGVV |
| 7 | APP672-706 (Aβ1-35) | DAEFRHDSGYEVHHQKLVFFAEDVGSNKGAIIGLM |
| 8 | APP672-708 (Aβ1-37) | DAEFRHDSGYEVHHQKLVFFAEDVGSNKGAIIGLMVG |
| 9 | APP672-709 (Aβ1-38) | DAEFRHDSGYEVHHQKLVFFAEDVGSNKGAIIGLMVGG |
| 10 | APP674-711 (Aβ3-40) | EFRHDSGYEVHHQKLVFFAEDVGSNKGAIIGLMVGGVV |
| 11 | APP672-710 (Aβ1-39) | DAEFRHDSGYEVHHQKLVFFAEDVGSNKGAIIGLMVGGV |
| 12 | APP672-711 (Aβ1-40) | DAEFRHDSGYEVHHQKLVFFAEDVGSNKGAIIGLMVGGVV |
| 13 | OxAPP672-711 (OxAβ1-40) | DAEFRHDSGYEVHHQKLVFFAEDVGSNKGAIIGL<u>M</u>VGGVV |
| 14 | APP671-711 | MDAEFRHDSGYEVHHQKLVFFAEDVGSNKGAIIGLMVGGVV |
| 15 | APP669-709 | VKMDAEFRHDSGYEVHHQKLVFFAEDVGSNKGAIIGLMVGG |
| 16 | APP672-713 (Aβ1-42) | DAEFRHDSGYEVHHQKLVFFAEDVGSNKGAIIGLMVGGVVIA |
| 17 | APP669-710 | VKMDAEFRHDSGYEVHHQKLVFFAEDVGSNKGAIIGLMVGGV |
| 18 | APP669-711 | VKMDAEFRHDSGYEVHHQKLVFFAEDVGSNKGAIIGLMVGGVV |
| 19 | APP666-709 | ISEVKMDAEFRHDSGYEVHHQKLVFFAEDVGSNKGAIIGLMVGG |
| 20 | APP666-711 | ISEVKMDAEFRHDSGYEVHHQKLVFFAEDVGSNKGAIIGLMVGGVV |

TABLE 1-continued

| SEQ ID NO. | Truncated APP variants | Sequence<br>TEEISEVKMDAEFRHDSGYEVHHQKLVFFAEDVGSNKGAIIGLMVGGVVIA<br>663                                                     713 |
|---|---|---|
| 21 | APP664-711 | EEISEVKMDAEFRHDSGYEVHHQKLVFFAEDVGSNKGAIIGLMVGGVV |
| 22 | APP663-711 | TEEISEVKMDAEFRHDSGYEVHHQKLVFFAEDVGSNKGAIIGLMVGGVV |

TABLE 2

| SEQ ID NO. | Theoretical average mass | Measured average mass in linear TOF | Theoretical monoisotopic mass | Measured monoisotopic mass in QIT reflectron TOF | Observed fragmentation at c-terminal side of Asp or Glu in MS/MS spectrum | Mascot score |
|---|---|---|---|---|---|---|
| 1 | 3152.7 | 3153.5 | 3150.68 | 3150.89 | $b_{12}$, $b_{13}$, $y_{17}$, $y_{18}$ | 5 |
| 2 | 3514.0 | 3513.5 | 3511.74 | 3511.92 | $b_{17}$, $b_{18}$, $y_{15}$, $y_{31}$ | 27 |
| 3 | 3613.1 | 3613.1 | 3610.82 | 3610.93 | $b_{17}$, $b_{18}$, $y_{16}$ | 22 |
| 4 | 3675.0 | 3677.0 | 3672.78 | 3672.85 | $b_{22}$, $b_{23}$, $y_{22}$, $y_{26}$ | 5 |
| 5 | 3712.2 | 3711.8 | 3709.88 | 3709.99 | $b_{17}$, $b_{18}$, $y_{17}$, $y_{18}$, $y_{33}$ | 33 |
| 6 | 3868.4 | 3868.1 | 3865.98 | 3866.06 | $b_{19}$, $y_{18}$, $y_{33}$ | 11 |
| 7 | 3919.4 | 3918.1 | 3916.91 | 3916.95 | $b_{22}$, $b_{23}$, $y_{12}$, $y_{28}$ | 6 |
| 8 | 4075.6 | 4074.8 | 4073.00 | 4072.93 | $b_{22}$, $b_{23}$, $y_{14}$, $y_{30}$, $y_{36}$ | 14 |
| 9 | 4132.6 | 4132.4 | 4130.02 | 4129.89 | $b_{11}$, $b_{22}$, $b_{23}$, $y_{31}$, $y_{35}$, $y_{37}$ | 22 |
| 10 | 4144.7 | 4144.7 | 4142.09 | 4142.08 | $b_9$, $b_{20}$, $b_{21}$, $y_{17}$, $y_{33}$ | 9 |
| 11 | 4231.8 | 4231.7 | 4229.09 | 4229.20 | $b_{11}$, $b_{22}$, $y_{32}$ | 13 |
| 12 | 4330.9 | 4330.6 | 4328.16 | 4328.11 | $b_{11}$, $b_{22}$, $b_{23}$, $y_{17}$, $y_{29}$, $y_{33}$, $y_{37}$, $y_{39}$ | 90 |
| 13 | 4346.9 | 4346.6 | 4344.16 | 4343.99 | $b_{11}$, $b_{22}$, $b_{23}$, $y_{33}$, $y_{39}$ | 14 |
| 14 | 4462.1 | 4462.0 | 4459.20 | 4459.40 | $b_{23}$, $b_{24}$, $y_{17}$, $y_{29}$, $y_{33}$, $y_{39}$ | 8 |
| 15 | 4491.1 | 4491.6 | 4488.22 | 4488.15 | $b_{10}$, $b_{14}$, $b_{26}$, $y_{35}$ | 15 |
| 16 | 4515.1 | 4514.8 | 4512.28 | 4512.35 | $b_{11}$, $b_{22}$, $b_{23}$, $y_{35}$ | 17 |
| 17 | 4590.3 | 4590.2 | 4587.29 | 4587.06 | $b_9$, $b_{13}$, $b_{25}$, $y_{33}$, $y_{39}$ | 11 |
| 18 | 4689.4 | 4689.0 | 4686.36 | 4686.19 | $b_{10}$, $b_{14}$, $b_{25}$, $b_{26}$, $y_{33}$, $y_{37}$ | 17 |
| 19 | 4820.5 | 4818.2 | 4817.38 | 4817.27 | $b_{13}$, $y_{31}$, $y_{37}$ | N/I |
| 20 | 5018.7 | 5018.7 | 5015.52 | 5015.28 | $b_{13}$, $b_{28}$, $b_{29}$, $y_{39}$ | 17 |
| 21 | 5277.0 | 5276.9 | 5273.60 | N/D | N/A | N/A |
| 22 | 5378.1 | 5378.7 | 5374.65 | N/D | N/A | N/A |

In Tables 1 to 2, OxAPP672-711 (OxAβ1-40) represented by SEQ ID NO: 17 indicates a peptide oxidized at Met 706 in APP672-711 (Aβ1-40) represented by SEQ ID NO: 16. "N/D" means "not detected". "N/A" means out of application of MS/MS analysis.

The invention claimed is:

1. A method for measuring amyloid precursor protein (APP) cleavage peptides in a blood sample, the method comprising the steps of:
bringing a blood sample into contact with an antibody-immobilizing carrier in a binding solution to bind the antibody-immobilizing carrier and APP cleavage peptides contained in the blood sample, the antibody-immobilizing carrier including a carrier, and an antibody bound to the carrier and selected from the group consisting of an immunoglobulin having an antigen binding site capable of recognizing amyloid precursor protein (APP) cleavage peptides and an immunoglobulin fragment containing an antigen binding site capable of recognizing amyloid precursor protein (APP) cleavage peptides, wherein said binding solution contains n-Dodecyl-β-D-maltoside (DDM) and n-Nonyl-β-D-thiomaltoside (NTM), and said binding solution has a surfactant concentration of 0.05 to 2%;
washing a bound body of the antibody-immobilizing carrier and the APP cleavage peptides using a washing solution, wherein said washing solution contains n-Dodecyl-β-D-maltoside (DDM) and n-Nonyl-β-D-thiomaltoside (NTM);
dissociating the APP cleavage peptides from the antibody-immobilizing carrier using an acidic aqueous solution containing an organic solvent and eluting the dissociated APP cleavage peptides; and
detecting the dissociated and eluted APP cleavage peptides.

2. The method according to claim 1, wherein a concentration of the organic solvent in the acidic aqueous solution is 25 to 70% (v/v).

3. The method according to claim 1, wherein in the detecting step, detection by mass spectrometry is conducted.

4. The method according to claim 3, wherein in the mass spectrometry, a matrix-assisted laser desorption/ionization mass spectrometer is used.

5. The method according to claim 4, wherein in the matrix-assisted laser desorption/ionization mass spectrometer, a matrix in a concentration of 0.1 to 20 mg/mL is used.

6. The method according to claim 4, wherein in the matrix-assisted laser desorption/ionization mass spectrometer, a matrix comprising at least one selected from the group consisting of α-cyano-4-hydroxycinnamic acid (CHCA), 2,5-dihydroxybenzoic acid (2,5-DHB), sinapic acid, and 3-aminoquinoline (3-AQ) is used.

7. The method according to claim 4, wherein in the matrix-assisted laser desorption/ionization mass spectrometer, a matrix solvent comprising at least one selected from the group consisting of acetonitrile (ACN), trifluoroacetic acid (TFA), methanol, ethanol and water is used.

8. The method according to claim 4, wherein in the matrix-assisted laser desorption/ionization mass spectrometer, a matrix additive is used, wherein the matrix additive comprises at least one selected from the group consisting of phosphonic acid, methylphosphonic acid, phenylphosphonic acid, 1-naphthylmethylphosphonic acid, methylenediphosphonic acid (MDPNA), ethylenediphosphonic acid, ethane-1-hydroxy-1,1-diphosphonic acid, nitrilotriphosphonic acid, and ethylenediaminetetraphosphonic acid.

9. The method according to claim 4, wherein in the matrix-assisted laser desorption/ionization mass spectrometer, a matrix additive prepared as a solution of 0.1 to 10 w/v % in water or in a matrix solvent is used.

10. The method according to claim 1, wherein the acidic aqueous solution for dissociating the APP cleavage peptides comprises hydrochloric acid as a buffer and 25%-70% (v/v) of acetonitrile as the organic solvent.

11. The method according to claim 1, wherein the APP cleavage peptides comprise Aβ1-40.

12. The method according to claim 1, wherein the APP cleavage peptides comprise Aβ1-42.

13. The method according to claim 1, wherein the carrier comprises at least one material selected from the group consisting of agarose, dextran, silica gel, polyacrylamide, polystyrene, polyethylene, polypropylene, polyester, polyacrylonitrile, (meth)acrylic acid polymer, fluororesin, metal complex resin, glass, metal, and a magnetic substance.

14. The method according to claim 1, wherein the antibody is bound to the carrier via a spacer.

15. The method according to claim 1, wherein prior to bringing the blood sample into contact with the antibody-immobilizing carrier in a binding solution, IgG and IgM contained in the blood sample are removed.

16. The method according to claim 1, wherein the washing solution further comprises ammonium ions.

17. The method according to claim 16, a concentration of ammonium ion in the washing solution is 5 to 1,000 mM.

18. The method according to claim 1, wherein the washing solution has pH 6.5 to 8.5.

19. The method according to claim 1, wherein the washing comprises subjecting a carrier surface to a fluid pressure of 0.01 to 500 MPa of the washing solution.

20. The method according to claim 1, wherein the carrier is a planar carrier, and washing comprises spraying a high-pressure washing liquid from a washing nozzle.

\* \* \* \* \*